US009433698B2

(12) United States Patent
Ingber et al.

(10) Patent No.: US 9,433,698 B2
(45) Date of Patent: Sep. 6, 2016

(54) HIGH STRENGTH CHITIN COMPOSITE MATERIAL AND METHOD OF MAKING

(75) Inventors: Donald E. Ingber, Boston, MA (US); Javier Gomez Fernandez, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 311 days.

(21) Appl. No.: 13/819,391

(22) PCT Filed: Aug. 30, 2011

(86) PCT No.: PCT/US2011/049702
§ 371 (c)(1),
(2), (4) Date: Jul. 8, 2013

(87) PCT Pub. No.: WO2012/030805
PCT Pub. Date: Mar. 8, 2012

(65) Prior Publication Data
US 2013/0287836 A1     Oct. 31, 2013

Related U.S. Application Data

(60) Provisional application No. 61/378,056, filed on Aug. 30, 2010.

(51) Int. Cl.
| | |
|---|---|
| A61L 15/22 | (2006.01) |
| B05D 3/10 | (2006.01) |
| C08L 5/08 | (2006.01) |
| A61L 27/22 | (2006.01) |
| A61L 27/34 | (2006.01) |
(Continued)

(52) U.S. Cl.
CPC ............. *A61L 15/225* (2013.01); *A61L 15/38* (2013.01); *A61L 15/425* (2013.01); *A61L 15/44* (2013.01); *A61L 15/52* (2013.01); *A61L 27/227* (2013.01); *A61L 27/34* (2013.01); *A61L 27/48* (2013.01); *A61L 27/54* (2013.01); *A61L 27/56* (2013.01); *B05D 3/104* (2013.01); *C08L 1/02* (2013.01); *C08L 3/02* (2013.01); *C08L 5/00* (2013.01); *C08L 5/08* (2013.01); *C08L 5/10* (2013.01); *C08L 89/00* (2013.01)

(58) Field of Classification Search
None
See application file for complete search history.

(56) References Cited

U.S. PATENT DOCUMENTS 5,245,012 A   9/1993   Lombari et al.
5,525,335 A   6/1996   Kitahara et al.
(Continued)

FOREIGN PATENT DOCUMENTS

CN   201143321    11/2008
CN   101411893    4/2009
(Continued)

OTHER PUBLICATIONS

Nogueira et al. "Layer-by-layer deposited chitosan/silk fibroin thin films with anisotropic nanofiber alignment." Langmuir, 26(11), pp. 8953-8958 (2010).
(Continued)

*Primary Examiner* — Bethany Barham
*Assistant Examiner* — Dominic Lazaro
(74) *Attorney, Agent, or Firm* — Nixon Peabody LLP

(57) ABSTRACT

The present invention is directed to a composite laminar material with high mechanical strength and methods of fabricating the material. The invention also provides a method of attaching a medical implant device to tissue.

13 Claims, 18 Drawing Sheets

(51) Int. Cl.

| | | |
|---|---|---|
| *A61L 27/48* | (2006.01) | |
| *A61L 27/54* | (2006.01) | |
| *A61L 27/56* | (2006.01) | |
| *A61L 15/38* | (2006.01) | |
| *A61L 15/42* | (2006.01) | |
| *A61L 15/44* | (2006.01) | |
| *A61L 15/52* | (2006.01) | |
| *C08L 1/02* | (2006.01) | |
| *C08L 3/02* | (2006.01) | |
| *C08L 5/00* | (2006.01) | |
| *C08L 5/10* | (2006.01) | |
| *C08L 89/00* | (2006.01) | |

(56) References Cited

U.S. PATENT DOCUMENTS

| | | | |
|---|---|---|---|
| 2002/0032414 A1* | 3/2002 | Ragheb et al. | 604/265 |
| 2003/0099630 A1 | 5/2003 | DiBenedetto et al. | |
| 2004/0005363 A1 | 1/2004 | Tsukada et al. | |
| 2004/0199241 A1 | 10/2004 | Gravett et al. | |
| 2008/0149561 A1* | 6/2008 | Chu et al. | 210/500.38 |
| 2008/0160856 A1* | 7/2008 | Chen et al. | 442/341 |
| 2008/0176960 A1* | 7/2008 | Tsukada et al. | 514/773 |

FOREIGN PATENT DOCUMENTS

| | | |
|---|---|---|
| EP | 0437095 A2 | 7/1991 |
| EP | 0 753 313 A1 | 1/1997 |
| JP | S5640156 A | 4/1981 |
| JP | 01254164 A | 10/1989 |
| JP | 2002291862 A | 10/2002 |
| JP | 2008137970 A | 6/2008 |
| KR | 10-2000-0051938 | 8/2000 |
| KR | 2010 0009305 A | 1/2010 |
| WO | 97/08315 | 3/1997 |
| WO | 0016817 A1 | 3/2000 |
| WO | 2005012606 A2 | 2/2005 |
| WO | 2006-027622 | 3/2006 |
| WO | 2008103017 A1 | 8/2008 |
| WO | 2009/100280 | 8/2009 |
| WO | 2010/042798 | 4/2010 |

OTHER PUBLICATIONS

Cai et al. "Surface engineering of titanium thin films with silk fibroin via layer-by-layer technique and its effects on osteoblast growth behavior." J. of Biomedical Materials Research Part A, 82A(4), pp. 927-935 (2007).

Lucas et al., "Advances in Protein Chemistry: The Silk Fibroins" Academic Press Inc., Publishers, New York, New York, pp. 107-242 (1958).

Liu et al., "Biomimetic Sealant Based on Gelatin and Microbial Transglutaminase: An Initial In Vivo Investigation", Journal of Biomedical Materials Research, Part B, Applied Biomaterials, 91(1):5-16 (2009).

* cited by examiner

HIGH STRENGTH CHITIN COMPOSITE MATERIAL AND METHOD OF MAKING

CROSS REFERENCE TO RELATED APPLICATIONS

This application is a 35 U.S.C. §371 National Phase Entry Application of International Application No. PCT/US2011/049702 filed Aug. 30, 2011, which designates the U.S., and which claims benefit under 35 U.S.C. 119(e) of U.S. Provisional Patent Application Ser. No. 61/378,056 filed Aug. 30, 2010, the content of which is incorporated herein by reference in its entirety.

FIELD OF THE INVENTION

The present invention is directed to an organic composite material formed from carbohydrates and proteins. More specifically, the invention relates to a composite biocompatible material formed from layers of Chitosan and proteins, such as Fibroin, having superior strength and energy-dissipating properties.

BACKGROUND OF THE INVENTION

Chitin is the second most abundant polymer on earth after cellulose, it is common waste in seafood factories and (as a natural polymer) it is biodegradable. However its processing in the laboratory for fabrication produce a hydrogel material with poor mechanical properties.

Chitin is a broadly employed polymer in nature. It is found in the walls of fungi, in mollusk shells and the exoskeleton of arthropods. It provides many structural uses due to its mechanical properties. Many attempts have carried out to employ the polymer as a substitute of current synthetic plastics; however it has not been possible to reproduce its exceptional natural properties in the lab. The lack of success results from the failure to appreciate the important structural role played by chitin-associated proteins that are present within natural structures, and the laminar microarchitecture of naturally occurring materials produced by living organisms.

The main protein present both in the mollusk shells and the arthropods exoskeleton, which plays a fundamental role in the structural integrity of the shell, has an amino acid sequence similar to that of silk fibroin.

Chitin and protein (such as silk fibroin) blends have been produced in the prior art by the simple mixing of both materials in solution. These processes are intent on producing consistent mixtures of Chitin/Chitosan and silk fibroin by mixing both polymers in solution and casting the mixture. That approach does not yield any improvement in the mechanical properties of mixture over the components, and typically produces an even weaker material due to the interaction of both polymers, which interferes with each other's molecular and crystal structure.

Silk Fibroin is well known polymer material. Silk provides an important set of material options for biomaterials and tissue engineering because of the impressive mechanical properties, biocompatibility and biodegradability. Silk polymer and Silk Fibroin includes silkworm fibroin and insect or spider silk protein (Lucas et al., Adv. Protein Chem 13: 107-242 (1958)). Preferably, fibroin is obtained from a solution containing a dissolved silkworm silk or spider silk. Generally, fibroin polymer (or protein) from silk has been treated to substantially remove sericin. The silkworm silk protein is obtained, for example, from *Bombyx mori*, and the spider silk is obtained, for example, from *Nephila clavipes*. In the alternative, silk proteins suitable for use in the present invention can be obtained from a solution containing a genetically engineered silk, such as from bacteria, yeast, mammalian cells, transgenic animals or transgenic plants. See, for example, WIPO Publication No. WO 1997/108315 and U.S. Pat. No. 5,245,012 which are hereby incorporated by reference herein.

Silk fibroin has excellent film-forming capabilities and is also compatible for use in the human body. Silk fibroin films, without further manipulation or treatment, are soluble in water because of dominating random coil protein structures. The structural features of the protein can be transformed from random coil to beta-sheet structure by several treatments, including mechanical stretching, immersion in polar organic solvents, or curing in water vapor. Without wishing to be bound by a theory, use of highly concentrated silk solutions is also known to promote beta-sheet transition from random coils. This structural transition results in aqueous insolubility, thus providing options for the use of the material in a range of biomedical and other applications. Some pure silk fibroin films tend, over time, to become stiff and brittle in the dry state, however, exhibiting impressive tensile strength but low ductility. Further, dissolved Silk Fibroin can be mixed with particulates to produce a homogeneous mixture that can be formed into implantable structures. Methods of making silk polymer structures and Silk Fibroin films are shown in WIPO Publication Nos. WO 2009/0100280 and WO 2010/0042798, both which are hereby incorporated by reference herein.

SUMMARY OF THE INVENTION

The invention relates to the process for the formation of complex 3D structures with a carbohydrate polymer, e.g., oligosaccharides and polysaccharides, with high control of shape, topography and material properties, and the resulting composite material. It also relates to the sequential modification of those structures with proteins for the improvement of specific characteristics, for example, the limitation of mechanical properties of the material by the use of silk fibroin and the coating of different regions of the material with water-resistant coatings to modify hydration. The resulting composite material has enhanced mechanical strength properties significantly greater than, and not predicted by, any of component materials.

In accordance with implementations of the invention, one or more of the following capabilities may be provided.

One object of the invention is to provide a method of fabricating a composite material formed from layers of a carbohydrate based polymer and a protein. For example, a composite material formed from layers of a Chitin-based material and a protein.

Another object of the invention is to provide a method of fabricating a composite material formed from layers of a carbohydrate based polymer and a Fibroin. For example, a method of fabricating a composite material formed from layers of Chitin-based material and Fibroin.

Another object of the invention is to provide a composite material formed from a carbohydrate based polymer and a protein having superior mechanical properties as compared to its component materials. For example, a composite material formed form a Chitin-based material and a protein having superior mechanical properties as compared to its component materials.

Another object of the invention is to provide a composite material formed from Chitosan and Fibroin having superior mechanical properties as compared to its component materials.

Another object of the invention is to provide a composite material formed from a carbohydrate based polymer and a protein having adjustable mechanical properties. For example, a composite material formed from a Chitin-based material and a protein having adjustable flexibility properties.

Another object of the invention is to provide a composite material formed from Chitosan and a protein having adjustable mechanical properties.

Another object of the invention is to provide a composite material formed from Chitosan and a protein that is biocompatible and biodegradable but stable in the presence of moisture.

These and other capabilities of the invention, along with the invention itself, will be more fully understood after a review of the following figures, detailed description, and claims.

BRIEF DESCRIPTION OF THE FIGURES

FIG. 23A shows an image of a piece of tissue covered by a chitosan-fibroin film enzymatically attached to the tissue (as in the inset). A trench in the tissue piece was made to show that the film can easily follow complex geometries. FIG. 23B shows the removal of the film by pulling (a T-peel test). The film is being removed from right to left. Inset show the principle of a T-peel test. FIG. 23C shows the resulting measurements from the t-peel test. FIG. 23D is a bar graph showing the average force necessary to peel a 1 cm wide film attached to the tissue by enzymatic adhesion (Shr+tTG), without any promoter, just the film over the tissue (Shr), the adhesive force of two pieces of tissue glued together by enzymatic adhesion (tTG), and the force of gluing a film with a cyanoacrylate based glue (aka "superglue") (Cyn). As seen, enzymatic adhesion (Shr+tTG) is not only clearly above the adhesion force of the natural tissue, but also very close to the cyanoacrylate adhesion force, while both the method and the materials are perfectly compatible and bioabsorbable.

In FIG. 25, Tg-1 to Tg-5: samples treated with transglutaminase; no Tg-2: sample not treated with a transglutaminase; and dermis+Tg: adhesion to dermis in presence of a transglutaminase. This shows that shrilk can be used as a "patch" in skin treatments (e.g., bandages).

DETAILED DESCRIPTION OF THE INVENTION

Figure 1:
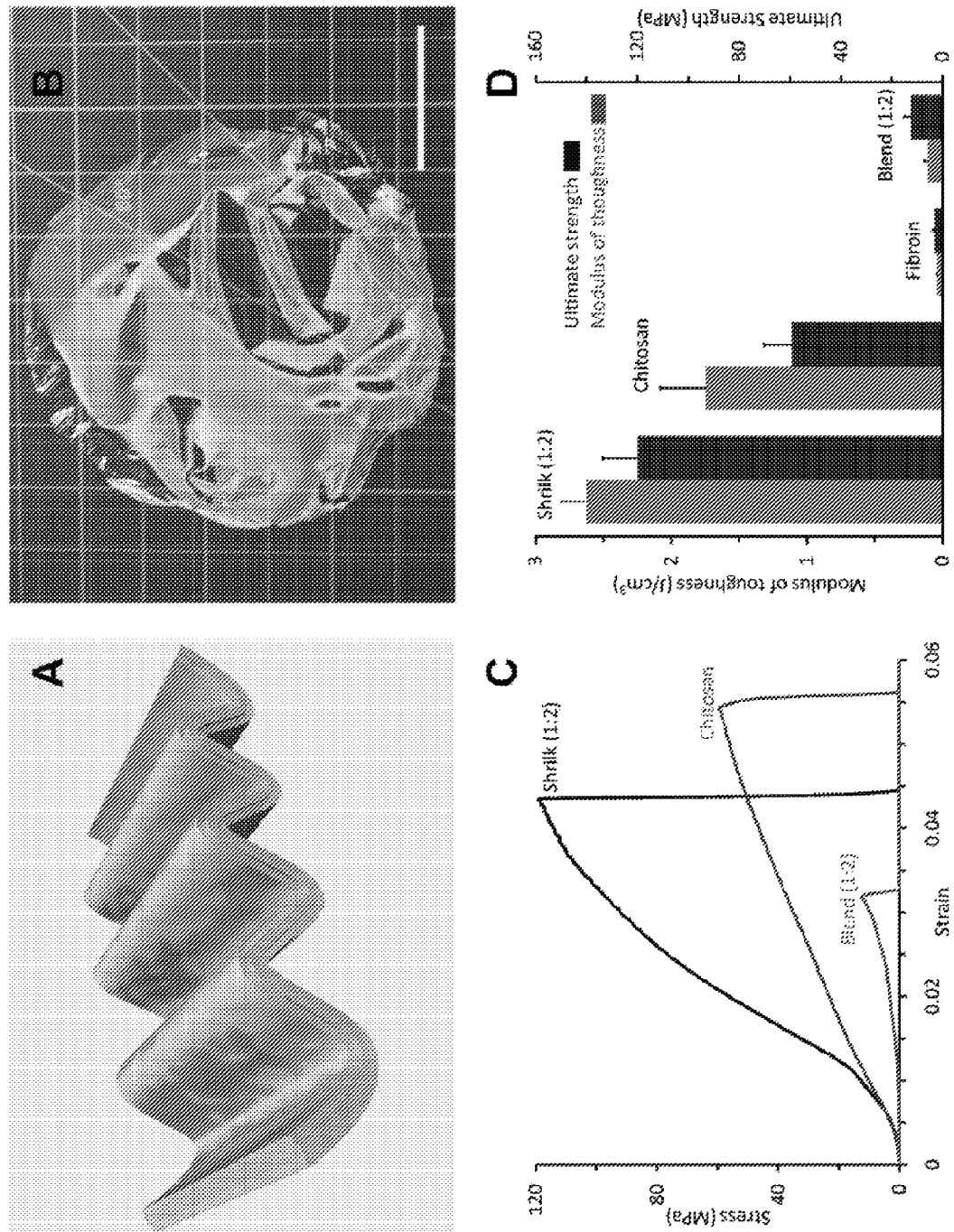
FIG. 1A shows a diagram of the composite material according to the invention, which mimics the natural laminar structure of insect cuticles and crustacean exoskeletons. A Chitosan film (blue) is merged with a separated Fibroin phase (yellow).
FIG. 1B shows a picture of a Chitosan-Fibroin film, called 'Shrilk', (bar is 2.3 cm) according to the present invention.
FIG. 1C shows representative stress-strain curves of the Shrilk composite laminate material (blue line, 1:2 weight ratio Chitosan:Fibroin), Chitosan alone (red line) and the 1:2 blend (mixture) of Chitosan:Fibroin.
FIG. 1D shows graphs of the Modulus of toughness (grey, left vertical axis) and breaking strength (black, right vertical axis) of the Shrilk composite material, Chitosan, Fibroin and the Fibroin-Chitosan blend (with SD error bars).

The present invention relates to a composite material formed from carbohydrate polymers, and one or more proteins and the process for the fabrication of these composite materials into useful structures. The present invention is directed to a composite material that includes layers of the component materials. In accordance with the invention, complex 3D structures with high control of shape, topography and material properties can be fabricated from the resulting composite material.

In some embodiments, the composite material has the structure $[(\text{protein-layer})_x:[(\text{carbohydrate-layer})_y:(\text{protein-layer})_z]_m]_n$, wherein m, n, y, and z are independently an integer equal to or greater than 1; and x is 0 or an integer equal to or greater than 1.

Generally, n, m, y, and z are independently an integer from 1 to $10^6$. For example, each of m, n, y and z can be independently 1, 2, 3, 4, 5, 6, 7, 8, 9, 10, 11, 12, 13, 14, 15, 16, 17, 18, 19, or 20. Similarly, x can be 0 or an integer from 1 to $10^6$. For example, x can be 0, 1, 2, 3, 4, 5, 6, 7, 8, 9, 10, 11, 12, 13, 14, 15, 16, 17, 18, 19, or 20

In some embodiments, the composite material comprises one or more of layers of carbohydrate-layer:protein-layer, e.g., m is 1, n is 1 to $10^6$, x is 0, y is 1, and z is 1, and the composite material has the structure [carbohydrate-layer:protein-layer]$_n$. In some embodiments, m is 1; n is 1, 2, 3, 4, 5, 6, 7, 8, or 9; x is 0; y is 1; and z is 1.

In some embodiments, the composite material comprises one carbohydrate-layer and one protein-layer, e.g., m, n, y, and z are 1 and x is 0, and the composite material has the structure carbohydrate-layer:protein-layer.

In some embodiments, the composite material comprises three carbohydrate-layers and three protein-layers, e.g., m, y, and z are 1; x is 0; and n is 3, and the composite material has the structure [carbohydrate-layer:protein-layer]$_3$.

In some embodiments, the outer most layer of the composite material is a protein-layer, e.g., m is 1 to $10^6$ and n, x, y, and z are all 1, and the composite material has the structure protein-layer:(carbohydrate-layer:protein-layer)$_m$.

In some embodiments, the composite material comprises one carbohydrate-layer and two protein-layers, e.g. m, n, x, y, and z are all one and the composite material has the structure protein-layer:carbohydrate-layer:protein-layer.

In some embodiments, the composite material comprises one carbohydrate-layer and two or more protein-layers, e.g., m is 1, n is 1 to $10^6$, x is 0, y is 1, and z is 2 to $10^6$, and the composite material has the structure [carbohydrate-layer:(protein-layer)$_z$]$_n$. In some embodiments, n is 1, x is 0, y is 1, and z is 2 to $10^6$, and the composite material has the structure carbohydrate-layer:(protein-layer)$_z$. In some embodiments, z is 2, 3, 4, 5, 6, 7, 8, 9, or 10.

In some embodiments, the composite material has the structure $[(\text{carbohydrate-layer})_p:[(\text{protein-layer})_q:(\text{carbohydrate-layer})_r]_t]_u$, wherein p, q, r, t, and u are independently an integer equal to or greater than 1.

Generally, p, q, r, t, and u are independently an integer from 1 to $10^6$. In some embodiments, p, q, r, t, and u are independently, 1, 2, 3, 4, 5, 4, 5, 6, 7, 8, 9, 10, 11, 12, 13, 14, 15, 16, 17, 18, 19 or 20.

In some embodiments, outer most layer of the composite material is a carbohydrate layer, e.g., p, q, r, and u are 1 and t is 1 to $10^6$, and the composite material has the structure carbohydrate-layer:[protein-layer:carbohydrate-layer]$_t$. In some embodiments, the composite material comprises two carbohydrate-layer and one protein-layers, e.g. p, q, r, t and u are all 1, and the composite material has the structure carbohydrate-layer:protein-layer:carbohydrate-layer.

The carbohydrate and the protein layers can be coextensive with each other or not coextensive. In other words, full surface of the carbohydrate layer can be coated with the protein layer or only a part of the surface of the carbohydrate layer can be coated with the protein layer.

In accordance with one embodiment of the invention, the sequential modification of the component carbohydrate based materials and the fabrication of composite structure with proteins can provide for the improvement of specific characteristics. In some embodiments, the resulting composite material has mechanical strength properties significantly greater than any of the component. In some embodiments, the mechanical strength of the composite material of the invention is at least 2-fold, at least 3-fold, at least 4-fold, at least 5-fold, at least 10-fold, at least 15-fold, at least 20-fold, at least 25-fold, at least 30-fold, at least 40-fold, at least 50-fold, at least 100-fold, at least 200-fold, at least greater than the mechanical strength of any one of the component materials.

In some embodiments, the mechanical strength of the composite material of the invention is at least 1.2-fold, at least 1.5-fold, at least 10.75-fold, at least 2-fold, at least 3-fold, at least 4-fold, at least 5-fold, at least 10-fold, at least 15-fold, at least 20-fold, at least 25-fold, at least 30-fold, at least 40-fold, at least 50-fold, at least 100-fold, at least 200-fold, at least greater than the total mechanical strength of the component materials.

Additionally, the composite material of the invention has very low density. In some embodiments, the density of the composite material is less than 2 g/cm$^3$, less than 1.9 g/cm$^3$, less than 1.8 g/cm$^3$, less than 1.7 g/cm$^3$, less than 1.6 g/cm$^3$, less than 1.5 g/cm$^3$, less than 1.4 g/cm$^3$, less than 1.3 g/cm$^3$, less than 1.2 g/cm$^3$, less than 1.1 g/cm$^{3'}$, less than 1 g/cm$^3$, less than 0.9 g/cm$^3$, less than 0.8 g/cm$^3$, less than 0.7 g/cm$^3$, less than 0.6 g/cm$^3$, less than 0.5 g/cm$^3$, less than 0.4 g/cm$^3$, less than 0.3 g/cm$^3$, less than 0.2 g/cm$^3$, less than 0.1 g/cm$^3$, or less than 0.05 g/cm$^3$.

Density of the composite material can be calculated as described in the ASTM specification D792-00. According to the ASTM specification standard D792-00, the density of the composite material (p) in g/cm$^3$ is:

$$\rho = \frac{W_a}{W_a + W_w - W_b}(\rho_{water})$$

where: $W_a$ is the weight of the specimen when hung in the air; $W_w$ is the weight of the partly immersed wire holding the specimen; $W_b$ is the weight of the specimen when immersed fully in distilled water, along with the partly immersed wire holding the specimen; and $\rho_{water}$ is the density in g/cm$^3$ of the distilled water at testing temperature (for example 0.9975 g/cm$^3$ at 23° C.). While the above is discussed in relation to water, other liquids can be used in place of water. Alternatively, or in addition to the above, the density-gradient techniques for measuring the density of plastics can be employed as described in ASTM specification D1505.

Density of the composite material can be determined at any suitable temperature and pressure. In some embodiments, density of the composite material is determined at a temperature in the range of 0° C. to 25° C. For example, density can be determined at 0° C., 5° C., 10° C., 15° C., 20° C., or 25° C. In some embodiments, density of the composite material is determined at a pressure of 100 kPa or 101.325 kPa.

In some embodiments, density of the composite material is at standard condition for temperature and pressure. Without any limitations, the standard condition for temperature and pressure can be those as defined by the International Union of Pure and Applied Chemistry (IUPAC) or the National Institute of Standards and Technology (NIST). The current version of IUPAC's standard is a temperature of 0° C. and an absolute pressure of 100 kPa, while NIST's version is a temperature of 20° C. and an absolute pressure of 101.325 kPa.

In some embodiments, density is measured at 0° C. and 100 kPa, at 0° C. and 101.325 kPa, at 15° C. and 101.325 kPa, at 20° C. and 101.325 kPa, at 25° C. and 101.325 kPa, at 25° C. and 100 kPa, at 20° C. and 100 kPa, at 15° C. and 100 kPa, or at 20° C. and 101.3 kPa.

In some embodiments, the composite material comprises an outer waterproof coating. As used herein, the term "waterproof" refers to a barrier against both liquid and gaseous water (i.e., against both liquid water and water vapor). Generally, the waterproof coating has a permeability of less than less than 1 as determined by the Water Vapor Transmission Test ASTME96. Exemplary water-repelling materials include, but are not limited to, parylene, polydimethylsiloxane, polyethylene, polyvinyl, polypropylene, polyester, latex, oils, organic solvents, waxes, lipids, esters of fatty acids, esters of sterols, long chain alcohols, myricyl palmitate, cetyl palmitate, lanolin, candelila wax, ouricury wax, sugarcane wax, retamo wax, jojoba oil, paraffin, and any combinations thereof.

The composite material can be coated with a waterproof layer by submerging the composite material in an organic solution (e.g., solution of a water-repelling material), and/or by protecting some regions from hydration (e.g., by microcontact printing patterns of water-repelling wax materials on the surface of the composite material), and permitting it in others. Generally, the organic solution will have an affinity for the carbohydrate and/or protein-layer. In some embodiments, the organic solution comprises wax or wax and a protein. Alternatively, the composite material can be waterproofed by depositing a layer of waterproofing material on at least one surface of the composite material. In some embodiments, the composite material is coated by vapor deposition of a waterproofing material. The waterproofing material also can be patterned to create regions that are susceptible to water contact adjacent to regions that are not susceptible to water contact to create a composite material that varies in its mechanical properties and degradability over its surface.

In some embodiments, at least one surface of the composite material comprises a outer coating (e.g., one or more layers) of parylene. Parylene is the trade name for a variety of chemical vapor deposited poly(p-xylylene) polymers, which are USP Class VI biocompatible polymers. Exemplary parylenes include, but are not limited to, parylene A, AF-4, AM, C, D, E, HT, N, SF, and X. Of the three most common types of parylene (C, D and N), parylene C is the most widely used in industry. The advantages of the use of parylene include its proven biocompatibility, its strength and flexibility (e.g., Young's modulus=4 GPa), its conformal pinhole-free room-temperature deposition, its low dielectric constant (=3) and high volume resistivity (>1016 Q-cm), its transparency, and its ease of manipulation using standard microfabrication techniques. Thus, parylene coating can be used to create a biocompatible, waterproof coating on the composite material. The paralyene coating can be patterned to create regions that are hydrophobic or biocompatible adjacent to regions that are not hydrophilic or not biocompatible. Without wishing to be bound by a theory, this can create a composite material that varies in its biocompatibility, mechanical properties, or degradability over its surface.

Carbohydrate Polymers

As used herein, the term "carbohydrate based polymer," includes, but is not limited to, oligomers or polymers that contain monomers having the formula $C_m(H_2O)_n$ wherein m and n are >3 and where in m and n can be same or different. Preferably m and n are independently 3, 4, 5, 6, or 7. Carbohydrate based polymers include, but are not limited to, compounds such as oligosaccharides, polysaccharides, glycoproteins, glycolipids and the like.

In some embodiments of this and other aspects of the invention, the carbohydrate polymer comprises at least 5, at least 6, at least 7, at least 8, at least 9, or at least 10 or sugar monomers.

Without limitation, the carbohydrate polymer comprises sugar monomers independently selected from the group consisting of erythrose, threose, ribose, arabinose, xylose, lyxose, ribulose, xylulose, allose, altrose, glucose, mannose, gulose, idose, galactose, galactosamine, N-acetylgalactose, glucosamine, N-acetylglucosamine, sialic acid, talose, psicose, fructose, sorbose, tagatose, fucose, fuculose, rhamonse, sedoheptulose, octose, sulfoquinovose and nonose (neuraminic acid), wherein the sugar may be optionally substituted. Without limitation each sugar can independently have the L- or the D-conformation.

The linkage between two sugar monomers can independently have the α- or β-configuration. Furthermore, the linkage between the two sugar can be 1→3, 1→4, 1→5, or 1→6.

In some embodiments, at least one (e.g., 1, 2, 3, or 4) hydroxyl of the sugar monomer is replaced by an amino group. In some embodiments, the hydroxyl at position 2 of the sugar monomer is replaced by an amino group. The amino group can be optionally substituted with an $C_1$-$C_6$ alkyl or an acyl group. Preferred $C_1$-$C_6$ alkyl groups include methyl, ethyl, propyl, butyl, and t-butyl. One preferred acyl group is acetyl.

In some embodiments of this and other aspects of the invention, the carbohydrate polymer comprises one or more (e.g., 1, 2, 3, 4, 5, 6, 7, 8, 9, or 10 or more) disaccharide, trisaccharide or tetrasaccharide monomers independently selected from the group consisting of sucrose, lactulose, lactose, maltose, trehalose, cellobiose, kojibiose, nigerose, isomaltose, β,β-Trehalose, α,β-Trehalose, sophorose, laminaribiose, gentibiose, turanose, maltulose, palatinose, gentibiulose, mannobiose, melibiose, rutinose, rutinulose, xylobiose, raffinose, melezitose, acarbose and stachyose.

As used herein, the term "oligosaccharide" refers without limitation to several (e.g., five to ten) covalently linked monosaccharide units. As used herein, the term "polysaccharide" refers without limitation to many (e.g., eleven or more) covalently linked sugar units. Polysaccharides can have molecular masses ranging well into millions of daltons. Exemplary oligosaccharides and polysaccharides include, but are not limited to, fructooligosaccharide, galactooligosaccharides, mannanoligosaccharides, glycogen, starch (amylase, amylopectin), glycosaminoglycans (e.g., hyaluronic acid, chondroitin-4-sulfate, chondroitin-6-sulfate, dermatan sulfate, keratin sulfate, heparin and the like), cellulose, beta-glucan (zymosan, lentinan, sizofiran), maltodextrin, inulin, levan beta (2→6), chitin, and chitosan.

In some embodiments of this and other aspects of the invention, the carbohydrate polymer is chitin or a derivative thereof. One preferred chitin derivative is chitosan (α-(1-4) 2-amino-2-deoxy-β-D-glucan) and derivatives thereof. Exemplary derivatives of chitosan include, but are not limited to, N-(aminoalkyl) chitosans, succinyl chitosans, quteraminated chiotosans, N-acylated chitosans (e.g., caproyl chitosan, octanoyl chitosan, myristoyl chitosan, and palmitoyl chitosan), N-methylene phosphonic chitosans, N-lauryl-N-methylene phosphonic chitosans, N-lauryl-carboxymethyl chitosans, N-alkyl-O-sulfated chitosans, thiolated chitosans (e.g., chitosan-2-iminthiolane, chitosan-4-thiobutylamidine, and chitosan-thioglycolic acid), and phosphorylated chitosans).

One of skill in the art is well aware of synthetic methods which can be used for the synthesis of carbohydrate polymers. See for example, Stick, R. V., *Carbohydrates: The Sweet Molecules of Life*.; Academic Press, pp 113-177 (2002); Crich, D. & Dudkin V., *J. Am. Chem. Soc.*, 123: 6819-6825 (2001); Garegg, P. J., *Chemtracts-Org. Chem.*, 5:389 (1992); Mayer, T. G., Kratzer, B. & Schmidt, R. R. Synthesis of a GPI anchor of the yeast *Saccharomyces cerevisiae*. Angew. Chem. Int. Ed. Engl. 33, 2177-2181 (1994); Seifert, J., Lergenmuller, M. & Ito, Y. Synthesis of an α-(2,3)-sialylated complex-type undecasaccharide. Angew. Chem. Int. Ed. 39, 531-534 (2000); Wang, Z.-G. et al. Toward fully synthetic homogeneous glycoproteins: a high mannose core containing glycopeptide containing carrying full H-type 2 human blood group specifity. Angew. Chem. Int. Ed. 40, 1728-1732 (2001); Caruthers, M. H. Gene synthesis machines: DNA chemistry and its uses. Science 230, 281-285 (1985); Sears, P. & Wong, C.-H. Toward automated synthesis of oligosaccharides and glycoproteins. Science 291, 2344-2350 (2001); Zhang, Z. et al. Programmable one-pot oligosaccharide synthesis. J. Am. Chem. Soc. 121, 734-753 (1999; Nishimura, S. Automated glycosynthesizer 'Golgi' by mimicking biosynthetic process. Tanpakushitsu Kakusan Koso 48, 1220-1225 (2003); Plante, O. J., Palmacci, E. R. & Seeberger, P. H. Automated solid-phase synthesis of oligosaccharides. Science 291, 1523-1527 (2001); Andrade, R. B., Plante, O. J., Melean, L. G. & Seeberger, P. H. Solid-phase oligosaccharide synthesis: preparation of complex structures using a novel linker and different glycosylating agents. Org. Lett. 1, 1811-1814 (1999); Love, K. R. & Seeberger, P. H. Automated solid-phase synthesis of protected tumor-associated antigen and blood group determinant oligosaccharides. Angew. Chem. Int. Ed. 43, 602-605 (2004); and Seeberger, P. H. & Werz, D. B. Synthesis and medical applications of oligosaccharides. Nature 446, 1046-1051 (2007), content of all of which is herein incorporated by reference.

Proteins

Generally any protein that can be induced to form an ordered structure, e.g., from random coil and/or helical structure to β-sheet, can be used in the fabrication of the composite material of the invention. A protein can be transformed from a random coil to a β-sheet form by treatment with heating, mechanical stretching, immersion in organic solvents, e.g., ethanol, methanol, and curing in water vapor. See for example, Hu et al., 41 Macromolecules 3939-48 (2008); Jin & Kaplan, 424 Nature 1057-61 (2003); Canetti et al., 28 Biopolymers—Peptide Sci. §1613-24 (1989); and Jin et al., 15 Adv. Funct. Mat. 1241-47 (2005), content of all which is incorporated herein by reference. In some cases, using a highly concentrated protein solutions can also promote beta-sheet transition from random coils. Without wishing to be bound by a theory, this structural transition results in aqueous insolubility, thus providing options for the use of such material in a range of biomedical and other applications such as sensor platforms. See for example Zhang, 16 Biotechnol. Adv. 961-71 (1998), content of which is incorporated herein by reference.

In some embodiments, the protein is a silk protein or an analog or a derivative thereof. In some embodiments, the silk protein is fibroin. Silk protein can be a naturally occurring silk protein, e.g. silk extracted from silkworm cocoons, or a silk like protein or polymer. A number of silk like proteins and polymers are known in the art and are amenable to the present invention. See for example Asakura et al., Production and characterization of a silk-like hybrid protein, based on the polyalanine region of *Sarnia cynthia ricini* silk fibroin and a cell adhesive region derived from fibronectin, *Biomaterials*, 25(4): 617-624 (2004); Yang, M. & Kawamura, J. Development of silk-like materials based on *Bombyx mori* and *Nephila clavipes* dragline silk fibroins, Polymer, 50(1): 117-124 (2009); Barr, L. A., Fahnestock S. R., & Yang, J. Production and purification of recombinant DP1B silk-like protein in plants, *Molecular Breeding*, 13(4): 345-356 (2004); Anderson, J. P., Cappello, J., & Martin, D.C. Morphology and primary crystal structure of a silk-like protein polymer synthesized by genetically engineered *Escherichia coli* bacteria, *Biopolymers*, 34(8): 1049-1058 (2004); Huang, J. Foo, C. W. P., & Kaplan, D. L. Biosynthesis and Applications of Silk-like and Collagen-like Proteins, *Polymer Reviews*, 47(1) 29-62 (2007); Yao, J. & Asakura, T. Synthesis and Structural Characterization of Silk-Like Materials Incorporated with an Elastic Motif, *J. Biochem.* 133(1): 1147-1154 (2003); Yang et al., Silklike materials constructed from sequences of *Bombyx mori* silk fibroin, fibronectin, and elastin, *J. Biomed. Mater. Res. Part A*, 84A(2): 353-363 (2007); and Werten et al., Biosynthesis of an Amphiphilic Silk-Like Polymer, *Biomacromolecules*, 9(7): 1705-1711 (2008), content of all of which is herein incorporated by reference. Hardy and Scheible presented a review of the silk inspired polymers and proteins, Hardy, J. G. & Scheibel, T. R. *Biochem. Soc. Trans.* 36: 677-681 (2009), content of which is herein incorporated by reference.

Without wishing to be bound by a theory, silk fibroin has excellent film-forming capabilities and is also biocompatible and acceptable for use in the human body. Altman et al., 24 Biomats. 401-16 (2003); Vepari & Kaplan, 32 Prog. Polym. Sci. 991-1007 (2007). Silk fibroin films have good dissolved oxygen permeability in the wet state, similar to that of human skin, which suggests potential applications for these films in wound dressing and artificial skin systems. Minoura et al., 11 Biomats., 430-34 (1990); Minoura et al., 31 Polymer, 265-69 (1990a). Films formed from silk fibroin, without further manipulation, are soluble in water, however, because of dominating random coil protein structures.

Furthermore, the structural features of silk fibroin can be transformed from random coil to β-sheet form by treatment with heating, mechanical stretching, immersion in organic solvents, e.g., ethanol, methanol, and curing in water vapor. Silk fibroin can also be induced to form beta-sheets by using highly concentrated fibroin solution.

In some embodiments of the aspects described herein, the protein is selected from the group consisting of perculin, abductin, fibrin, fibroin, elastin, resilin, fibronectin, fibrinogen, keratin, titin, collagen, actin, Arp2/3, coronin, dystrophin, FtsZ, myosin, spectrin, Tau (protein), tubulin, F-spondin, Pikachurin, protein fragments, synthetic peptides, genetically expressed portions of proteins, fragments thereof, and any combinations thereof.

The characteristics of the composite material can be modulated, e.g., enhanced, by using a protein other than silk proteins or silk like proteins, mixture of proteins, and/or by incorporating non-protein molecules in the protein-layer. For example, elastin or resilin can be used for the protein-layer, or added to carbohydrate-layer and/or protein-layer to increase elasticity. Similarly perlucin can be used for the protein-layer, or added to carbohydrate-layer and/or protein-layer to improve mineralization.

In some embodiments of the aspects described herein, the composite material comprises a molecule selected from the group consisting of carbon fibers, carbon nanotubes, fiberglass, small molecules, polymers, proteins, peptides, peptidomimimetics, nucleic acids, organic compounds, inorganic compounds, crystalline compounds, biological compounds, biologically active compounds, compounds having biological activity, and a biological, a pharmaceutical or a therapeutic agent, and any combinations thereof, in at least one of carbohydrate-layer or protein-layer of the composite material.

Synthesis of Composite Material

The composite material of the invention can be prepared by preparing alternating layers of carbohydrate and protein-layers on a suitable surface. A carbohydrate based substrate, such as a film, can first be prepared by drying a carbohydrate solution (e.g. a carbohydrate polymer solution). In some embodiments, the carbohydrate based substrate is in a acid solution. Some exemplary acids include, but are not limited to, itaconic acid, polyitaconic acid, acontic acid, uric acid, glucuronic acid, formic acid, acetic acid, trichloroacetic acid, propionic acid, butanoic acid, 4-chlorobutanoic acid, 3-chlorobutanoic acid, 2-bromobutanoic acid, 2-chlorobutanoic acid, chlorous acid, hypochlorous acid, citric acid, gluconic acid, lactic acid, oxalic acid, tartaric acid, ascorbic acid, Meldrum's acid, hydrofluoric acid, hydrocyanic acid, hydrogens sulfide, orthophosphoric acid, sulfurous acid, carbonic acid, conjugate acid of a weak base. Without limitation, the concentration of acid in the solution can range from about 0.1% w/v to about 10% w/v. In some embodiments, the solution comprises from about 1% w/v to about 2% w/v of the acid. In some embodiments, the acid is a weak acid having an acid ionization constant (Ka) of less than $10^{-2}$ at 25° C. In some embodiments, the acid is acetic acid.

The prepared carbohydrate substrate can be washed and further modified and/or neutralized. Depending upon the specificity of the prepared substrate an acidic or basic solution can be used for the modification and/or neutralization of the substrate. Exemplary bases include, but are not limited to, sodium hydroxide, ammonium hydroxide, potassium hydroxide, calcium hydroxide, magnesium hydroxide, barium hydroxide, strontium hydroxide, lithium hydroxide, rubidium hydroxide, sodium carbonate, and ammonia. Without limitation concentration of base in neutralizing solution can range from about 0.1% w/v to about 10% w/v. In some embodiments, the solution comprises from about 4% w/v to about 6% w/v of the base. In some embodiments, the neutralizing solution is a pH buffer, e.g., a high pH carbonate buffer. By high pH buffer is meant a buffer having a pH higher than 7, 8, 9, 10, 11, or 12 or higher.

If required, any remaining water molecules from the carbohydrate substrate can be removed using methods known to one of skill in the art for such purposes. For example, the film can be washed with an organic solvent such as alcohol, e.g., methanol, ethanol, etc. Furthermore, methods of preparing carbohydrate films are well known in the art and can be used to prepare such films. See for example, Ito, R. & Matsuo, Y. Eds. *Handbook of Carbohydrate Polymers Development, Properties and Applications*, Nova Science Pub. Inc. (2010); and Richert et al., *Langmuir,* 20(2): 448-58 (2004), content of which is herein incorporated by reference.

The carbohydrate substrate then can be coated with a layer of protein by dipping it in a protein solution. Alternatively, the carbohydrate substrate can be coated with a layer of protein by depositing a layer of protein solution on it. Generally, any ratio of protein to carbohydrate, e.g., weight ratio or mole ratio, can be used in formatting the composite material. In some embodiment, the carbohydrate to protein ratio is 10:1 to 1:10. In some embodiments, carbohydrate to protein ratio is 5:1 to 1:5, 2.5:1 to 1:2.5, 1.15:1 to 1:1.15. In some embodiments, the ratio is 1:1.5 to 1:2.5. In some embodiments, the ratio is 1:2. The ratio can be based on dry weight or moles of carbohydrate and protein added to the solution for forming the respective layers.

Generally, the carbohydrate solution comprises from about 1% w/v to about 50% w/v of the carbohydrate polymer. In some embodiments, the carbohydrate solution comprises from about 1% w/v to about 25% w/v of the carbohydrate. In some embodiments, the carbohydrate solution comprises from about 2% w/v to about 6% w/v of the carbohydrate. Without wishing to be bound by a theory, in some embodiments, high concentration carbohydrate solutions are used. For example, in some embodiments, the carbohydrate solution comprises from about 50% w/v to about 95% w/v of the carbohydrate. In some embodiments, the carbohydrate solution comprises from about 75% w/v to about 85% w/v of the carbohydrate.

Similar to the carbohydrate solution, the protein solution comprises from about 1% w/v to about 50% w/v of the protein. In some embodiments, the protein solution comprises from about 1% w/v to about 25% w/v of the protein. In some embodiments, the protein solution comprises from about 2% w/v to about 6% w/v of the protein.

The protein-layer can be optionally treated to induce a change in the protein structure, e.g., from fibrous to crystalline, α-helical to β-sheet, and vice versa. For example, the protein-layer can be treated to induce formation of crystalline structure. In some embodiments, the protein-layer can be treated to induce formation of β-sheet or similar structures. In some embodiments, the protein-layer is treated to induce a β transition. Exemplary methods of inducing changes in protein structure include, but are limited to, using a high concentration solution of protein, heating, freezing, mechanical stretching, pressure, immersion or washing with organic solvents, e.g., ethanol, methanol, and curing in water vapor.

The protein-layer itself can be built by a layer-by-layer design. For example, the carbohydrate substrate can be coated with a first layer of protein. Such coated carbohydrate can then be coated with a second layer of same protein or a different protein. This process can be repeated until the total protein-layer reaches the proper thickness. After each coating with protein, the protein-layer can be optionally treated to induce a change in the protein structure as described above.

Generally, the composite material has a thickness of from about 1 to about 500 µm. In some embodiments, the composite material has a thickness of from about 1 to about 250 µm, from about 1 to about 150 µm, from about 1 to about 100 µm, from about 1 to about 75, from about 1 to about 50 µm, from about 1 to about 25 µm, from about 1 to about 20 µm, from about 1 to about 15 µm, from about 1 to about 10 µm, or from about 1 to about 5 µm.

Thickness of each carbohydrate and protein-layer in the composite material can independently range from a few angstroms to millimeters, e.g., from about 1 Å to about 5 mm. In some embodiments, thickness of the each carbohydrate-layer can independently range from about 1 to about 250 µm. In some embodiments, thickness of each carbohydrate-layer is selected independently from the group consisting of from about 1 to about 100 µm, from about 1 to about 75 µm, from about 1 to about 50 µm, from about 1 to about 40 µm, from about 1 to about 30 µm, from about 1 to about 25 µm, from about 1 to about 20 µm, from about 1 to about 15 µm, from about 1 to about 10 µm, and from about 1 to about 5 µm. In some embodiments, all carbohydrate-layers have the same thickness. In some embodiments, at least two carbohydrate-layers have different thickness.

Similarly, the thickness of the protein-layers in the composite material can also independently range from a few angstroms to millimeters, e.g., from about 1 Å to about 5 mm. In some embodiments, thickness of the each protein-layer is independently from about 1 to about 250 µm. In some embodiments, thickness of each protein-layer is selected independently from the group consisting of from about 1 to about 100 µm, from about 1 to about 75 µm, from about 1 to about 50 µm, from about 1 to about 40 µm, from about 1 to about 30 µm, from about 1 to about 25 µm, from about 1 to about 20 µm, from about 1 to about 15 µm, from about 1 to about 10 µm, and from about 1 to about 5 µm. In some embodiments, all protein-layers have the same thickness. In some embodiments, at least two protein-layers have different thickness.

In some embodiments, thickness of a protein-layer is about 0.1× to about 5× the thickness of a carbohydrate-layer. In some embodiments, thickness of a protein-layer is about 0.25×, about 0.5×, about 0.75×, about 1×, about 1.25×, about 1.5×, about 1.75×, about 2×, about 2.5×, or about 5× the thickness of a carbohydrate-layer of the composite material.

In some embodiments, all layers of the composite material have the same thickness. In some embodiments, at least two layers of the composite material have different thickness. The at least two layers with different thickness can be layers of the same component (e.g., carbohydrate layers or protein layers) or at least one of carbohydrate layer and at least one of protein layers.

In one non-limiting example, the composite material is formed by preparing a Chitosan film. The Chitosan film can be prepared by drying a solution of Chitosan in an acid, for example acetic acid, and then neutralizing the film, using for example, NaOH. The Chitosan film is optionally dehydrated using, for example, methanol which promotes the release of interchain water molecules. The resulting dried Chitosan film can become less hydratable and more brittle. However, combining the Chitosan film with a coating of protein, such as Fibroin, for example, by dipping the Chitosan film in a fibroin water solution and allowing the resulting composite material to dry, yields a composite laminar film having significantly improved strength characteristics. In accordance with one embodiment of the invention, when the Chitosan film is combined with Fibroin in a range from approximately 1:1 to 4:1 (preferably 2:1.5-2:1) (w/w) ratio of Fibroin:Chitosan, the resulting composite material exhibits significantly greater strength characteristics than Chitosan alone.

In accordance with an alternative embodiment of the invention, the composite material can be fabricated from a medium molecular weight Chitosan. The Chitosan material having a medium molecular weight and a high degree of deacetylation (Sigma Aldrich) can be dissolved at 2% w/v in 1% v/v acetic acid. The 6 ml of the resulting solution can be poured on a 9 cm diameter Petri dish and the solvent evaporated at 37° C. The resulting film can be submerged in NaOH 4% (w/v) for a time period ranging from 5-15 min., for example 10 minutes, to neutralize the protonated amino groups and avoid further dissolution. The resulting Chitosan films can be intensely washed in deionized (DI) water to remove the remaining NaOH and then optionally dried at 37° C. The final thickness of the Chitosan can be in the range from 7-13 µm, for example 10 µm.

Fabrication of the Chitosan-Fibroin Laminar Composite:

In accordance with one embodiment of the invention, Silk from *Bombyx Mori* already degummed, available from Mielke's Fiber Arts (USA) is used to form the protein-layer. The silk can be washed several times in DI water before being dissolved at 10% w/v in LiBr at 80% (w/v) at 60° C. for 6 hours. The dissolved silk can be dialyzed against water in a dialysis tube with a molecular weight cut off of 12-14 kDa (VWR Scientific, USA). The dialysis can be carried out for 3, 4 or 5 days with constant water replacements. The final concentration of fibroin can be measured by weighing (XS205, Mettler Toledo, USA). The resulting Fibroin concentration can be in the range of 2-6%, for example, about 4% (w/v). An alternate method for producing aqueous silk fibroin solution is described in detail in WIPO Publication Number WO 2005/012606 entitled "Concentrated Aqueous Silk Fibroin Solution and Uses Thereof," which is incorporated by reference herein.

The Fibroin solution can be deposited on the Chitosan film immobilized at the bottom of a 9 cm diameter Petri dish and dried at 37° C. The resulting composite film can be immersed in methanol for 25 to 35 min, for example, 30 min to force the beta transition of the protein (and prevent further dissolution) and washed with DI water. In other embodiments, the beta transition can be induced by other inducing agents, including alcohols, organic solvents, aqueous solutions, the application of pressure and/or heat.

FIGS. 1A and 1B show samples of the composite material in accordance with the invention. FIG. 1A shows a diagram of the composite material according to one embodiment of the invention where the Chitosan film (blue) is bonded to a layer of Fibroin (green), which mimics the natural laminar structure that provides insect cuticles and crustacean exoskeletons with their novel mechanical properties. FIG. 1B shows a picture of the composite laminar material, in this example a thin (15 µm) clear film (the bar is 2.3 cm).

Microtopography

In accordance with an embodiment of the invention, a predefined microtopography of the resulting composite films can be produced by the casting the protein solution between a Polydimethoxysilane (PDMS) mold (fabricated by polymer casting on a structured Silicon surface) and the flat carbohydrate-layer or film. The composite film is then treated to induce a change in the protein structure, e.g., from fibrous to crystalline, α-helical to β-sheet, and vice versa. For example, the protein-layer can be treated to induce formation of crystalline structure. In some embodiments, the protein-layer can be treated to induce formation of β-sheet or similar structures. In some embodiments, the protein-layer is treated to induce a β transition. The composite material can be dried and peeled from the mold.

In a non-limiting example a predefined microtopography of the resulting composite films can be produced by the casting the Fibroin solution between a Polydimethoxysilane (PDMS) mold (fabricated by polymer casting on a structured Silicon surface) and the flat Chitosan film. The water can be evaporated at 37° C. for several hours, and the composite material peeled off from the mold. As in the case of non-structured composite material, the sample was methanol treated to force the beta transition and washed in DI water.

In accordance with an embodiment of the invention, the microtopography of the resulting composite films can be produced by depositing the protein on a structured carbohydrate film. The carbohydrate film can be structured by known methods, for example, by allowing a solution of carbohydrate to dry on a PDMS mold. The structured carbohydrate film then can be further treated as described herein to produce the structured composite material according to the invention.

In one non-limiting example, the microtopography of the resulting composite films can be produced by depositing the Fibroin protein on a structured Chitosan film. The Chitosan film can be structured by known methods, for example, by allowing the Chitosan in solution to dry on a PDMS mould. The structured Chitosan can be further treated as described herein to produce the structured composite material according to the invention.

Figure 3:
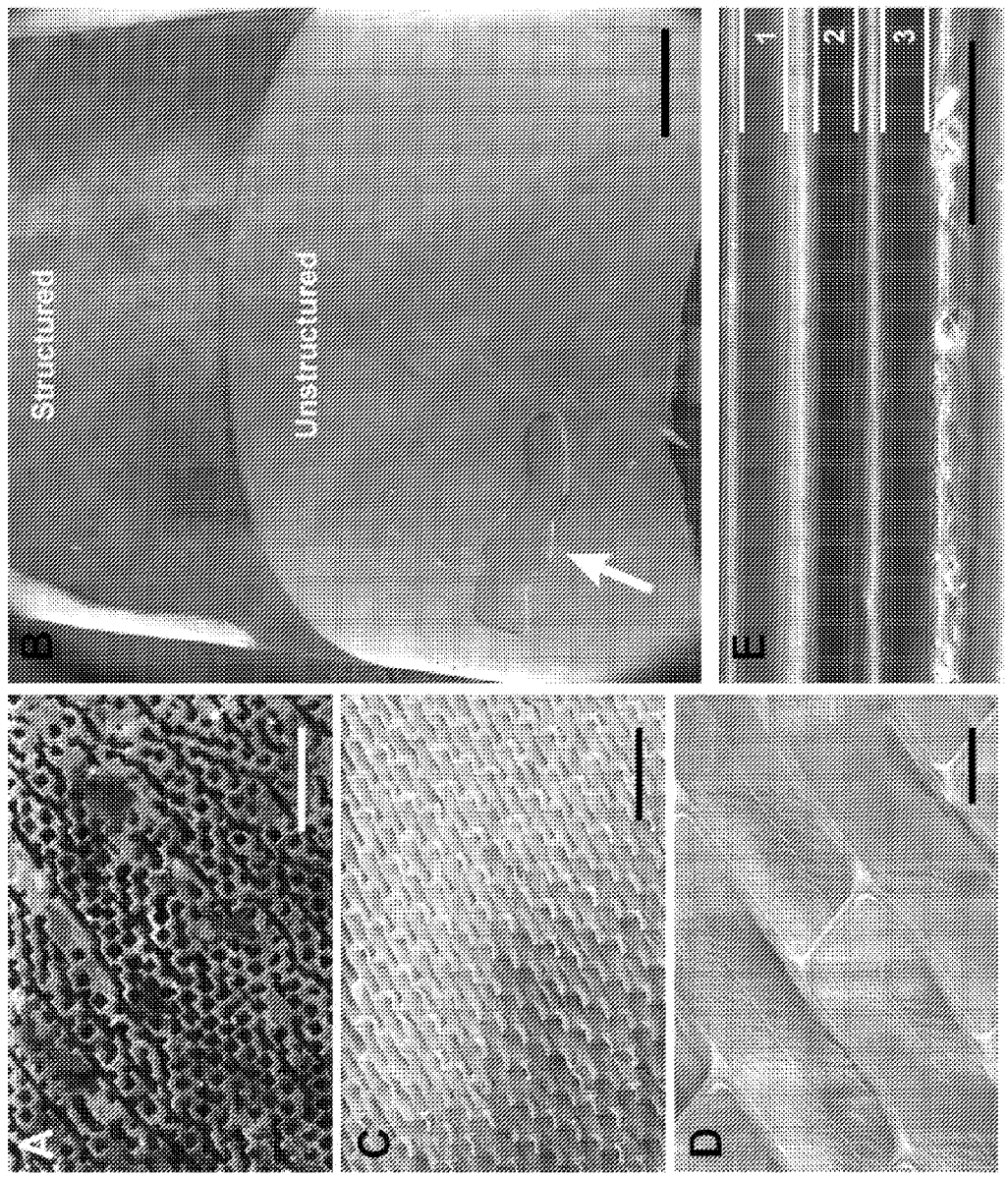
FIG. 3A shows the Topography of the Shrilk composite material fabricated by the deposition of the protein-layer on a microstructured Chitosan film (bar=100 μm) in accordance with the invention.
FIG. 3B shows a tube of the composite material with part of the surface microstructured. A region of the protein-layer has been compromised to form an open region (white arrow), which reveals the underlying Chitosan layer (bar=1 mm)
FIG. 3C shows surface microtopography of Shrilk where the structures are formed in the Fibroin protein-layer (bar=50 μm)
FIG. 3D shows structured surface, fabricated according to the invention, in more detail at higher magnification (bar=5 μm).
FIG. 3E shows a multi-laminate material containing multiple repeating layers of Chitosan and -Fibroin fabricated according to the invention (1,2, and 3 indicate 3 sequential layers of Chitosan-Fibroin laminates).

FIG. 3 shows the casting according to the embodiments of the invention. FIG. 3A shows the topography of the composite material formed according to the invention by the deposition of the protein phase on a structured Chitosan film (the bar=100 µm). FIG. 3B shows a tube of the composite material according to the invention with part of the surface structured and part of the surface unstructured. The white arrow points to an opening on the protein-layer that reveals the underlying Chitosan layer (the bar=1 mm). FIG. 3C shows the topography of the composite material formed according to an embodiment of the invention, where the structured surface is formed in the Fibroin (the bar=50 µm). FIG. 3D shows the structured surface of FIG. 3C in more detail. The horizontal bands on the walls are the replica of the deep reactive-ion etching marks of the mould (the bar=5 µm). FIG. 3E shows an SEM image of multiple layers of a multi-laminar composite Chitosan-Fibroin material formed in accordance with an embodiment of the invention. The numbers between lines refer to 3 different Chitosan layers (the bar=50 µm).

Stress/Strain Measurements

Samples of the dried composite material were cut in 1.5 cm wide by 8 cm long stripes and tested with Instron 3342 (500N, Instron, USA). The thickness of the samples was measured with microscopy (Axio Observer, Zeiss, Germany) as the average of 5 different points of the film. The thickness measurements were also corroborated in those samples subjected to SEM analysis.

FIG. 1C shows a stress-strain curve comparing the composite material according to the invention with the individual components. As shown, the strength of the composite Chitosan-Fibroin laminate material at a ratio of 1:2, herein called "Shrilk" is substantially greater than either Chitosan, or the non-laminar Chitosan-Fibroin blend that was produced by mixing Chitosan and Fibroin, both in liquid phase. The Fibroin films are very brittle (data is not shown in FIG. 1C), having a low breaking strength of 3.14 MPa (shown in FIG. 1C).

FIG. 1D shows the modulus of toughness and the breaking point of the composite Shrilk material and the component materials. As shown, both the modulus of toughness and breaking point of the composite laminar Shrilk material is substantially greater than either Chitosan, Fibroin or the unstructured Chitosan-Fibroin blend.

Figure 2:
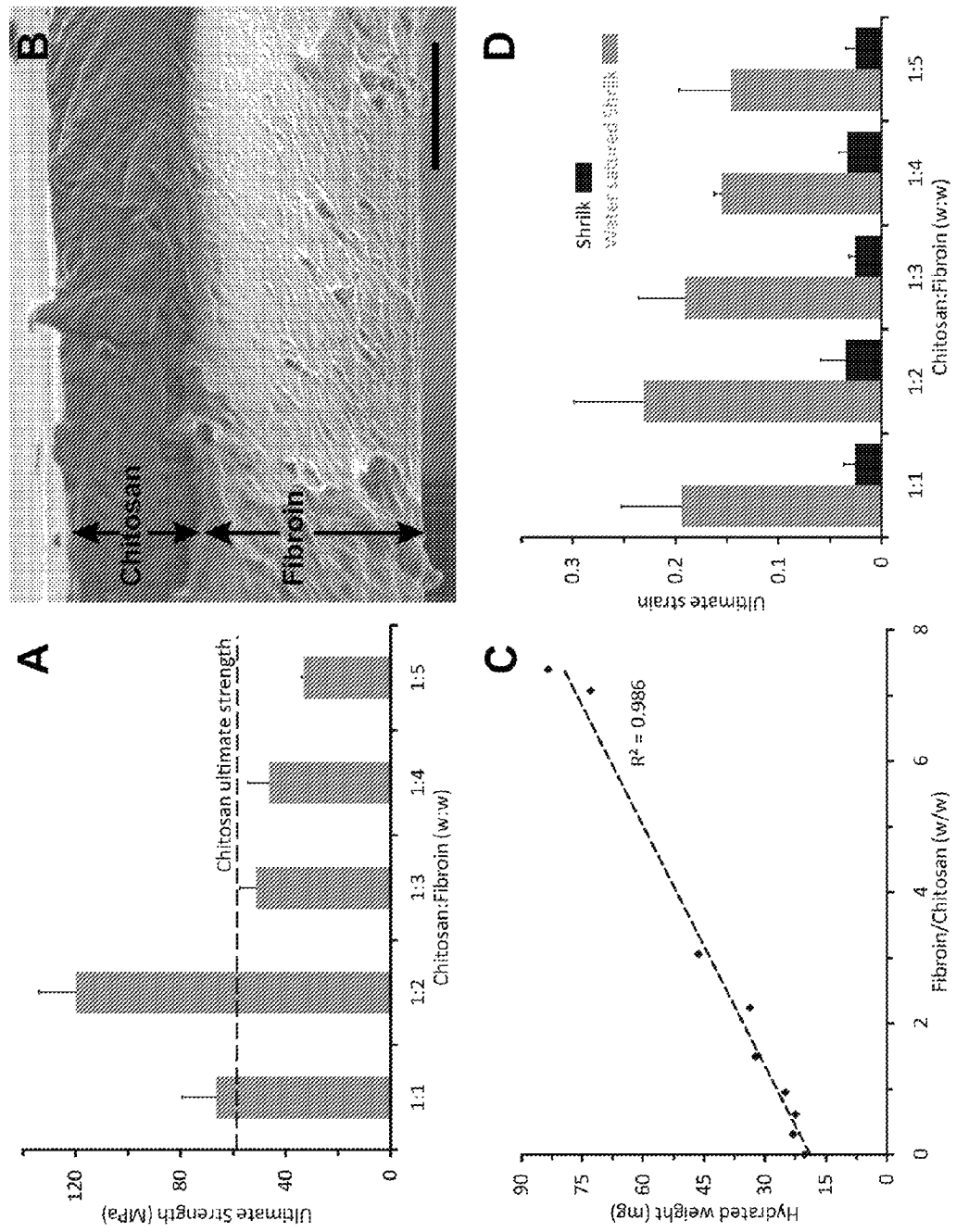
FIG. 2A shows the breaking strength of the Shrilk composite material fabricated according to the invention at different Chitosan:Fibroin ratios. Dashed line marks the breaking strength of the Chitosan film in absence of protein.
FIG. 2B shows a scanning electron micrograph (SEM) image of a Chitosan-Fibroin interface within the Shrilk laminate. The darker material (top) corresponds to the Chitosan layer, while the lighter one (bottom) is the fibroin layer (bar is 20 μm)
FIG. 2C shows a plot of the weight of the hydrated samples with respect the Fibroin:Chitosan content. The linear fit presumes independent absorption of each phase and indicates the lack of an effect of interactions between the polymer layers. The slope of the linear fit is 8.20 mg and the y-intercept is 18.89 mg.
FIG. 2D shows a graph of the mechanical strain at the break point (with SD error bars) for dry (red) and water-saturated (blue) Shrilk composite material fabricated according to the invention.

FIG. 2A shows the strength characteristics as a function of the ratio of Chitosan to Fibroin in the composite laminar material. FIG. 2A shows that breaking strength of the composite material is significantly greater than the breaking strength of Chitosan alone when the Chitosan to Fibroin ratio is 1:2. FIG. 2B shows an SEM image of the Chitosan-Fibroin interface within the laminar composite.

As indicated above, the composite material fabricated in accordance with the invention has the same components and amounts as the blend, however, the composite material, that mimics natural structures (such as in insect cuticles), is almost ten times stronger. Moreover, surprisingly the association of the Chitosan and Fibroin in the specific configuration of "Shrilk" composite laminar material is almost twice as strong as the strongest of the components (i.e. Chitosan). The energy per volume which each material is able to absorb before breaking (i.e. modulus of toughness, FIG. 1D) further illustrates unexpected properties of the Chitin/protein composites in accordance with the invention. While it could be expected that the addition of a very brittle material, such as Fibroin, to Chitosan would produce a material weaker than the Chitosan but stronger than Fibroin (e.g. the blend), the resulting "Shrilk" composite laminar material absorbs 1.5 times more energy than Chitosan before breaking.

Accordingly, the composite material can absorb at least 1.2-fold, at least 1.3-fold, at least 1.4-fold, at least 1.5-fold, at least 2-fold, at least 3-fold, at least 4-fold, at least 5-fold, at least 10-fold, at least 50-fold, at least 100-fold more energy than the constituent carbohydrate film before breaking.

In comparison with common materials, the ultimate strength of 120 Mpa of the composite material is twice that of Nylon and comparable to the Aluminum. However, because the composite material's density is approximately 1.46 g/cm$^3$, the Chitosan-Fibroin composite 'Shrilk' materials exhibit similar mechanical characteristics to Aluminum alloys and equivalents, but at half of the weight. In addition, Shrilk is biocompatible and biodegradable; in certain configurations, it is also optically clear.

Accordingly, the composite material can be at least 1.2-fold, at least 1.3-fold, at least 1.4-fold, at least 1.5-fold, at least 2-fold, at least 3-fold, at least 4-fold, at least 5-fold, at least 10-fold, at least 50-fold, at least 100-fold or more, stronger than the material formed from constituent carbohydrate or protein alone or a blend thereof. In some embodiments, the composite material has a strength of at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa or more.

In Shrilk, the maximum strength of the composite is approached when the weight ratio of Chitosan:Fibroin is approximately 1:2 (FIG. 2A). Increasing the amount of protein above certain limits does not appear to enhance the effect of the association; moreover, it has been observed that increasing the protein above the 1:2 ratio appears to nullify the effect of the design, giving rise to a material mechanically closer to Fibroin.

In SEM images of the Fibroin/Chitosan interface (FIG. 2B), the boundary is clearly defined by the different electronic properties of the materials but there is no other evidence of separation, confirming the high chemical affinity of both components.

While the composite material is discussed in terms of a carbohydrate film coated with a protein layer, the carbohydrate layer can be in a form other than a film. Accordingly, in some embodiments, the carbohydrate layer can be in the form of a foam, sponge, fiber, mesh or a nanoscale structure.

The composite material according to the embodiments of the invention can be fabricated into a foam-like or sponge-like material by injecting air bubbles into the carbohydrate solution as it dries, or using leachable materials (e.g., salt crystals) that can be dissolve after the foam or sponge is formed. Alternatively, the foam or sponge structure can be formed by freeze drying the carbohydrate solution. The sublimation of the solvent nucleates the bubbles that produce the porous structure of the foam or sponge. There are many ways to control the size of the pores. For example, the size of the pores can be controlled by controlling the temperature during freeze drying, varying the solvent concentration, and the like. The formed carbohydrate foam or sponge can then be immersed in a solution of protein or otherwise coated with a protein solution to produce a foam-like or sponge-like structure of the composite material. Without limitations, only a part or all of the carbohydrate based foam or sponge can be coated with the protein.

Further information concerning the formation of porous carbohydrate materials can be found, for example, in Madihally, S. V. & Matthew, H. W. T. Porous Chitosan scaffolds for tissue engineering. *Biomaterials,* 20(12): 1133-1142 (1999); and Xu, H. H. K & Simon, C. G. Fast setting calcium phosphate-Chitosan scaffold: mechanical properties and biocompatibility. *Biomaterials,* 26(12): 1337-1348 (2005), content of both of which is herein incorporated by reference. Another interesting option for forming foams is the use of high pressure $CO_2$ (i.e. supercritical $CO_2$) with the solid material. It mostly works by introducing $CO_2$ in the molecular structure by increasing the pressure, generally in the range 20 Bar. When the pressure is released, the $CO_2$ produce cavitation of the material. This method is of increasing popularity and considered "green".

The resulting foam or sponge can be mineralized by the introduction of crystalline materials, such as calcium carbonate, by immersing the composite material foam or sponge structure in a supersaturated solution of the crystalline material and allowing crystals to form on the surface and in the cavities.

In a non-limiting example, the composite material according to the embodiments of the invention can be fabricated into a foam-like or sponge-like material by injecting air bubbles into the Chitosan solution as it dries, or using leachable materials (e.g., salt crystals) that can be dissolved after the foam or sponge is formed. In accordance with embodiments of the invention, the Chitosan foam sponge can be immersed or otherwise coated with a Fibroin solution to produce a foam-like structure of the composite material. The resulting foam can be mineralized by the introduction of crystalline materials, such as Calcium Carbonate, by immersing the composite material foam structure in a supersaturated solution of calcium carbonate in water and allowing crystals to form on the surface and in the cavities of the foam. In one embodiment of the invention, an arbitrarily large amount of $CaCO_3$ is dissolved in water and subject to 20 psi of $CO_2$ for 1-3 days. After the pressure is released, the resulting liquid is filtered to remove the undissolved $CaCO_3$. After the solution returns to room temperature, the Chitosan foam or sponge (or film) can be immersed in the $CaCO_3$ solution.

In another non-limiting example, the foam or sponge structure can be formed by freeze drying the Chitosan dissolved in solution. The sublimation of the solvent nucleates the bubbles that produce the porous structure of the foam or sponge. There are many ways to control the size of the pores. For example, the size of the pores can be controlled by controlling the temperature during freeze drying. Alternatively, the size of the pores can be controlled by varying the concentration of the solvent. For the structures shown in FIGS. 5 and 6, the Chitosan was dissolved in a 1% Acetic Acid solution as compared with the 2% Acetic Acid solution used to prepare Chitosan films. Further information concerning the formation of porous substrate materials can be found in Madihally, S. V. and H. W. T. Matthew, Porous Chitosan scaffolds for tissue engineering. Biomaterials, 1999. 20(12): p. 1133-1142 and Xu, H. H. K. and C. G. Simon, Fast setting calcium phosphate-Chitosan scaffold: mechanical properties and biocompatibility. Biomaterials, 2005. 26(12): p. 1337-1348, both of which are incorporated by reference herein.

Figure 5:
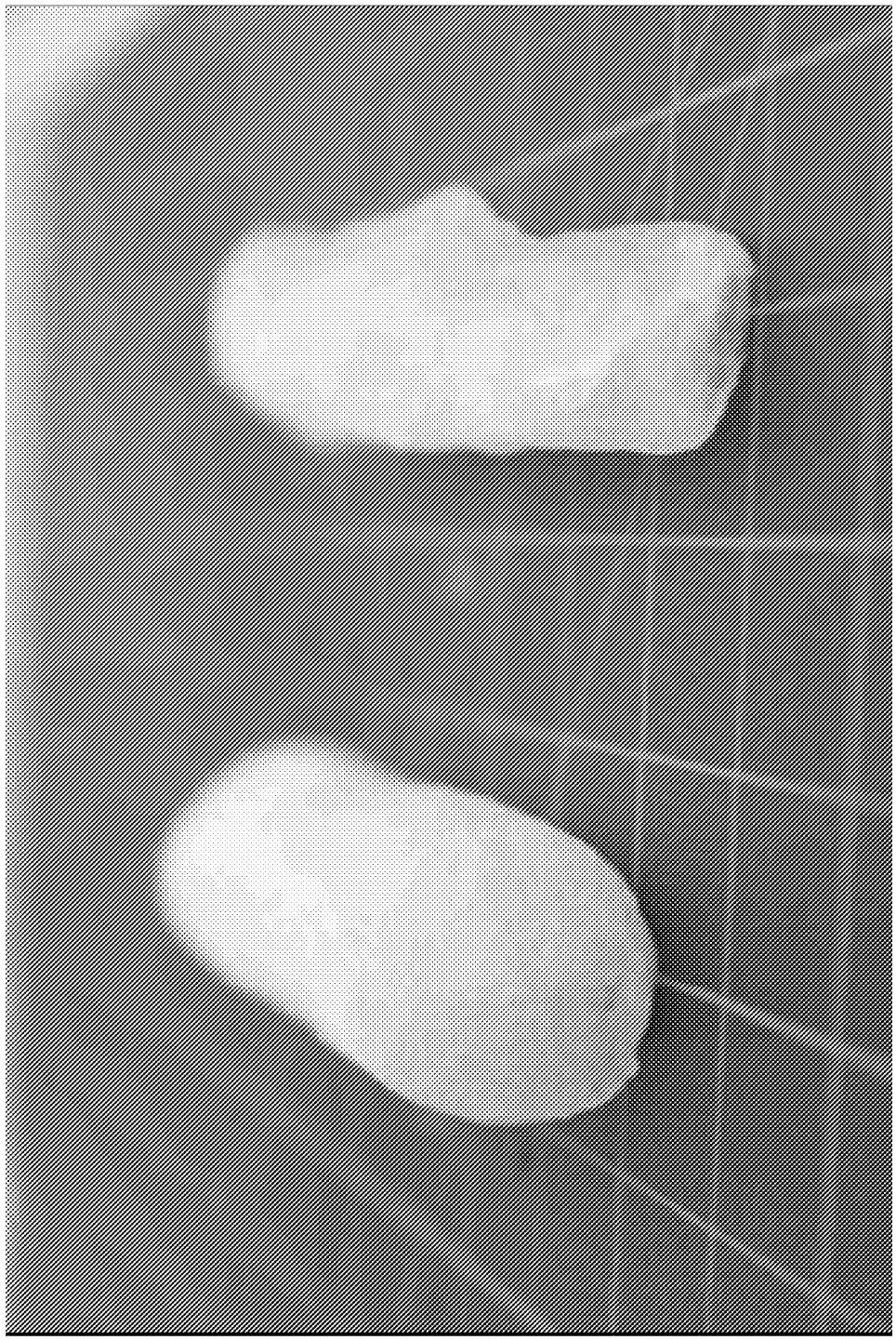
FIG. 5 shows a picture of a Shrilk composite material compared with Chitosan alone fabricated in a foam or sponge structure in the form of a cylinder.
Figure 6A:
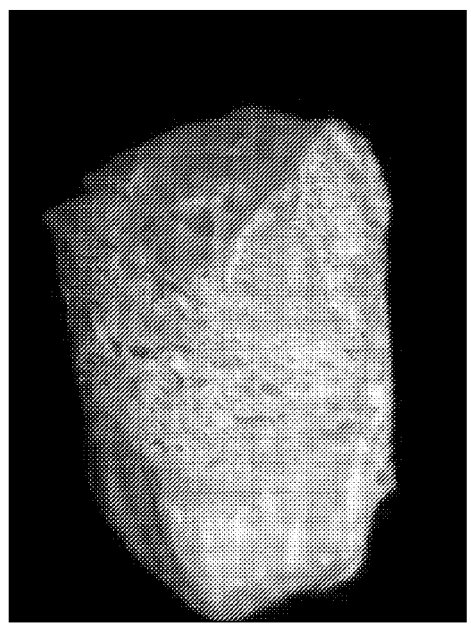
FIG. 6A shows a mineralized foam composite material structure fabricated according to the invention.
Figure 6B:
FIG. 6B shows an enlarged portion of the highly porous material from the inset of FIG. 6A.
Figure 7:
FIG. 7 shows pieces of tissue with different approaches for wound healing. Tissue has been bonded by the use of foams, films, or combinations of both.
Figure 8:
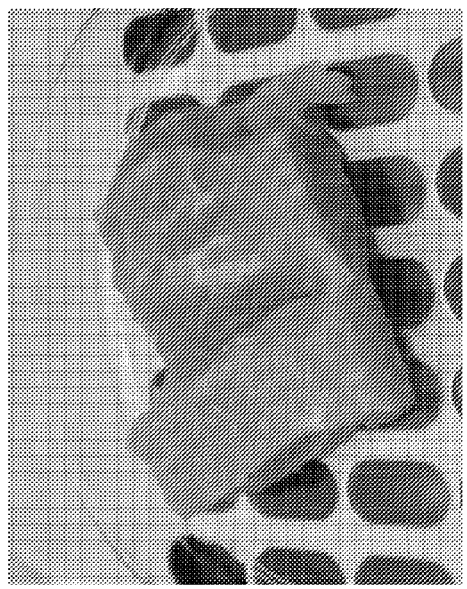
FIG. 8 shows pieces of tissue with an open cut.
Figure 9:
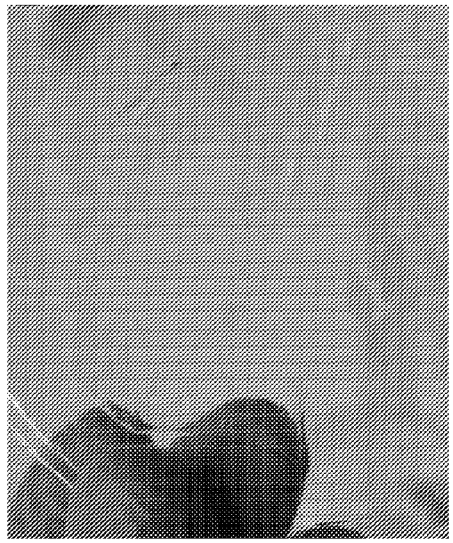
FIG. 9 shows chitosan based films (Shrilk) employed for bonding the separated pieces of tissue.
Figure 10:
FIG. 10 shows deposition of transglutaminase (i.e., white powder) over the tissue.
Figure 11:
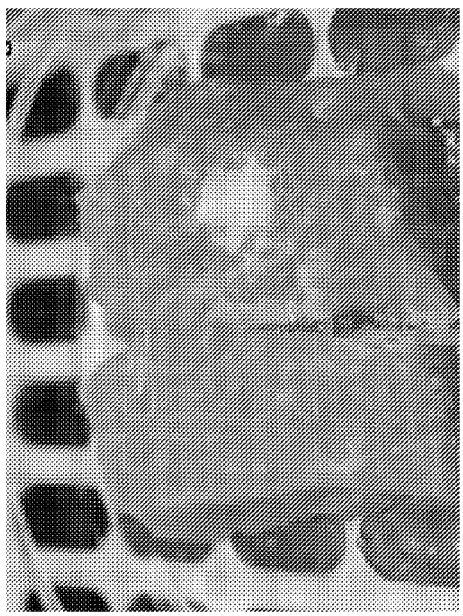
FIG. 11 shows closing of the tissue cut by the use of the chitosan based film of FIG. 9 on the transglutaminase treated tissue.
Figure 12:
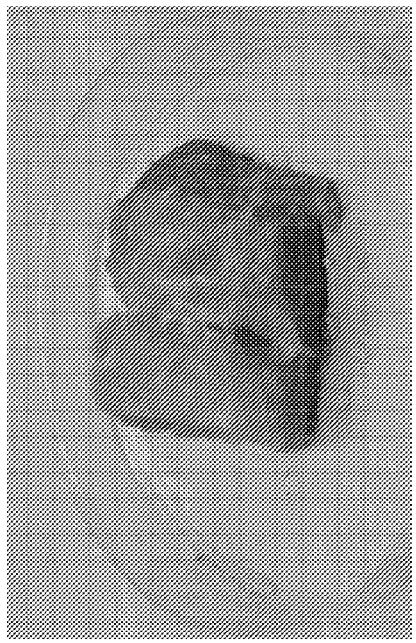
FIG. 12 shows the samples from FIG. 11 after three days.
Figure 13:
FIG. 13 shows sample following same procedure as for FIGS. 10-12 but with higher concentration of fat in the sample.
Figure 14:
FIG. 14 shows a traversal cut of the sample in FIG. 13 where the film can be clearly seen.
Figure 15:
FIG. 15 shows piece of tissue where a hole has been opened.
Figure 16:
FIG. 16 shows the sample from FIG. 15 with the transglutaminase treatment and the chitosan-based foam on top.
Figure 17:
FIG. 17 shows insertion of chitosan based piece of foam in the treated cavity.
Figure 18:
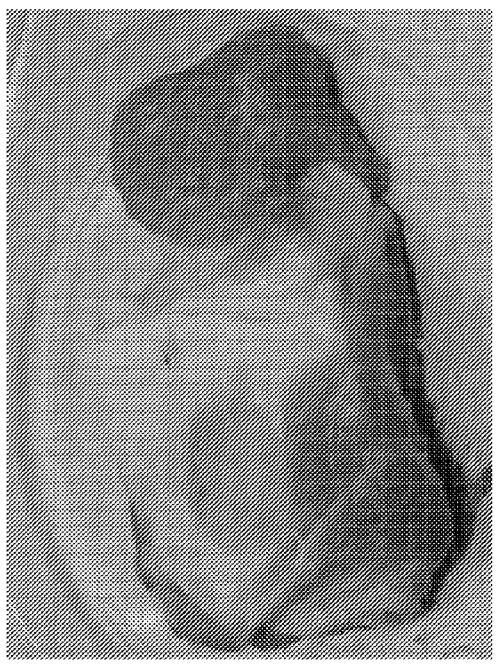
FIG. 18 shows the covering of the sample of FIG. 17 with a chitosan based film (similar to that in FIG. 9). The area under the chitosan film was also treated with transglutaminase to promote the crosslinking.
Figure 19:
FIG. 19 shows the same sample as in FIG. 18 but three days later. The sample was cut following the diameter of the cavity to observe the foam/tissue bond.
Figure 20:
FIG. 20 shows the same sample as in FIG. 19 but from a different angle.
Figure 21:
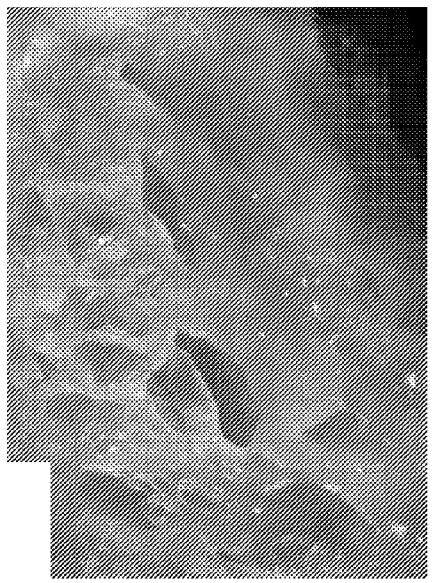
FIGS. 21 and 22 show closer images of the interface between the foam and the tissue. The film is also observed to be clearly attached to the foam.
Figure 22:
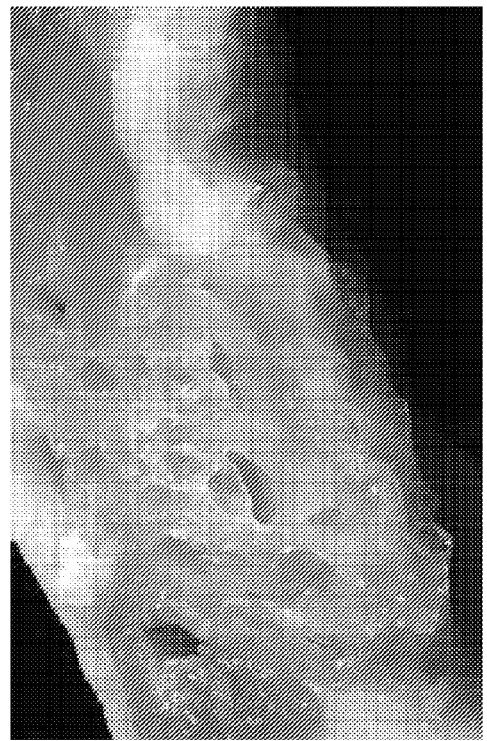

FIG. 5 shows samples of the composite material fabricated in a foam in accordance with the invention along side a Chitosan based foam structure in the form of a cylinder. FIGS. 6A and 6B show a mineralized foam composite material structure. FIG. 6B shows an enlargement of the inset in FIG. 6A in which the open pores of the structure are clearly visible.

In accordance with embodiments of the invention, the carbohydrate can be made into fibers by electrospinning—using an electric charge to produce fibers of carbohydrate polymer from a carbohydrate solution. For example, the carbohydrate fibers can be formed by injecting a solution of carbohydrates into a second solution such that the carbohydrate coagulates. The coagulate then can be extruded through a small diameter opening to control the diameter of the fiber. For example, a carbohydrate solution in acid can be injected into a basic solution or vice versa. Alternatively, coagulation can be induced by modulating the salt concentration of the solution, by chemical and/or mechanical means, such as pressure, heating or cooling, shaking etc. Further information concerning the formation of fibers can be found, for example, in Duan, B., C. Dong, X. Yuan, et al., Electrospinning of chitosansolutions in acetic acid with poly(ethylene oxide). *Journal of Biomaterials Science, Polymer Edition*, 15(6): 797-811 (2004) and Ohkawa, K., D. Cha, H. Kim, et al., Electrospinning of Chitosan. *Macromolecular Rapid Communications*, 25(18): 1600-1605 (2004), both of which are incorporated by reference herein. In an alternative embodiment of the invention, the carbohydrate can be formed into fibers by rotary jet spinning as described in "Nanofiber assembly by rotary jet-spinning," Badrossamay M R, McIlwee H A, Goss J A, Parker K K, Nano Lett. 2010 Jun. 9; 10(6):2257-6, which is hereby incorporated by reference.

In a non-limiting example, the Chitosan can be made into fibers by electrospinning—using an electric charge to produce fibers of Chitosan from a Chitosan solution. In accordance with one embodiment of the invention, fibers Chitosan can be formed by injecting a solution of Chitosan in acid (such as acetic acid) into a basic solution (such as NaOH). The Chitosan coagulates upon contact with the basic solution producing fibers of Chitosan. The coagulate can be extruded through a small diameter opening to control the diameter of the fiber. Alternatively, other fiber extrusion methods, such as rotary jet spinning, may be utilized (e.g., Mohammad Reza Badrossamay, Holly Alice McIlwee, Josue A. Goss, Kevin Kit Parker. Nanofiber Assembly by Rotary Jet-Spinning. *Nano Lett.*, 2010, 10 (6), pp 2257-2261).

In accordance with the present invention, the carbohydrate-layer can be formed with a defined topography at a nanoscale. The protein phase then can be applied over the defined nanoscale topography. Without wishing to be bound by theory, isotropic deposition and physical effects introduced by the topography (e.g., capillarity) produce degradation of the structures in defined regions. For example, Chitosan can be formed with a defined topography at a nanoscale with the protein phase applied over the structured Chitosan film. The result (FIG. 3A, same topography than B and C) shows that the isotropic deposition and the physical effects introduced by the topography (e.g. capillarity), produce degradation of the structures in defined regions even at very low Fibroin concentrations.

Proteins can also be used for fabricating microstructures by polymer casting. Accordingly, the microstructures can be formed by casting the protein-layer on a preformed microstructure. Additionally, the resulting composite material can be cast in a secondary shape by allowing the composite material to dry on the appropriate shape. For example, the composite material can cast into a tube by allowing the composite material to dry on a circular fixture or tube.

The composite material can be made flexible by exposure to water, either within localized regions or in whole, and then placed on a form or fixture to dry and set the secondary shape. By protecting some regions from hydration (e.g., by microcontact printing patterns of water-repelling wax materials on the surface of the composite material), and permitting it in others, the same composite laminar material can be made to exhibit variable material properties, such as more and less flexible regions based on the absorption of more and less water, respectively. Without wishing to be bound by theory, this mimics the mechanism by which the exoskeleton of anthropods gains its variable mechanical properties.

Fibroin is also a good material for the fabrication of microstructures by polymer casting. In accordance with embodiments of the invention, microstructures can be formed by casting the protein-layer as shown in FIGS. 3C and D. Additionally, the resulting composite material can be cast in a secondary shape, such as a tube (FIG. 3B) by allowing composite material to dry on a circular fixture or tube. Alternatively, the composite material can be made flexible by exposure to water, either within localized regions or in whole, and then placed on a form or fixture to dry and set the secondary shape. By protecting some regions from hydration (e.g., by microcontact printing patterns of water-repelling wax materials on the surface of the Shrilk), and permitting it in others, the same composite laminar material can be made to exhibit variable material properties, such as more and less flexible regions based on the absorption of more and less water, respectively. This mimics the mechanism by which the exoskeleton of anthropods gains its variable mechanical properties.

In accordance with the invention, the affinity between the components can be used to assemble separate composite material layers or structured components by "gluing" them with protein, e.g. Fibroin. This process allows multiple layers of the composite material to be built-up in order to fabricate complex three dimensional biocompatible structures. In some embodiments, carbohydrate components can be glued together by applying protein to dehydrated areas (or the entire surface) of the carbohydrate components and then causing a change in the protein structure, e.g., a β transition.

Accordingly, in an embodiment of the invention, Fibroin can be used to "glue" Chitosan structures. In this embodiment, Chitosan components can be glued together by applying Fibroin to dehydrated areas (or the entire surface) of Chitosan components and optionally causing the beta transition of the protein, such as by the application of alcohol, pressure or heat.

In accordance with an embodiment of the invention, a first layer of composite material (having a first layer of protein joined to a first layer of carbohydrate) can be joined to a second layer of composite material (having a second layer of protein jointed to a second layer of carbohydrate) by "gluing" using a low concentration protein solution ("gluing solution"). In some embodiments, gluing solution provides less than 1:2 carbohydrate to protein ratio. In some embodiments, the gluing solution comprises <4% w/v of protein. The two layers of composite material can be pressed together and any air bubbles removed, such as by using a straight edge or squeegee, to provide a substantially uniform layer of protein between the carbohydrate-layers. The resulting multilayer composite material can be allowed to dry, for example at 37° C. Additional materials of different types can be added into the glue layer (such as carbon fibers, carbon nanotubes, or other strong materials, particulates or fibers) to further increase material properties or optimize desired behavior of the laminate material.

In a non-limiting example, a first layer of composite material (having a first layer of Fibroin joined to a first layer of Chitosan) can be joined to a second layer of composite material (having a second layer of Fibroin jointed to a second layer of Chitosan) by "gluing" using a lower concentration (<4% w/v) Fibroin solution that provides less than the 2:1 Fibroin to Chitosan ratio. The two layers of composite material can be pressed together and any air bubbles removed, such as by using a straight edge or squeegee, to provide a substantially uniform layer of Fibroin between the layers of Chitosan. The resulting multilayer composite material can be allowed to dry, for example at 37 C. FIG. 3E shows an SEM cross section image of the multilayer composite material. The resulting structure has the mechanical characteristics of a single layer of composite material film (ultimate strength=116.7±12.3 MPa). As discussed above, additional materials of different types can be added into the glue layer (such as carbon fibers, carbon nanotubes, or other strong materials, particulates or fibers) to further increase material properties or optimize desired behavior of the laminate material.

Shrilk Composition: Chitosan/Protein/Water

Square samples of the chitosan/protein composite material, 2 cm on a side with a constant Chitosan thickness and variable amount of Fibroin, were weighed before being immersed in 37° C. DI water for 24 h. The linear approximation in FIG. 2C is made with the supposition that both phases are independent and the final weight of the composite material samples is given by:

$$W\text{wet} = W_{cs} A_{cs} + W_{fib} A_{fib} \qquad (i)$$

where: Wwet is the weight of the hydrated composite material, Wcs and Wfib are the dry weight of Chitosan and Fibroin in the sample, respectively, and Acs and Afib their associated water absorptions.

The inventors have also discovered that flexibility of the composite material can be modulated with water. Furthermore, the composite material can be reversibly transformed, by modulating the water content, from a very stiff material (when dry) to a flexible elastomer, independently of other factors such as tanning or composition. FIG. 2C shows the absorbance of water by the chitosan/protein composite material, providing a graph of the weight of the water saturated samples is represented against the Chitosan/Fibroin ratio. The water saturation is dependent on the volume rather that the surface and the final weight of the samples fits very well (R2=0.99) into the sum of the separate water uptake of both material layers; this indicates that water uptake is independent of the interaction between the components at the interface. Since the water absorbance of the Chitosan phase is 2.3 times higher than that of Fibroin, the samples with more Chitosan also contain more water, being the amount at equilibrium directly associated to concentration of the other two components.

Accordingly, in some embodiments of the aspects described herein, the composite material is hydrated. As used herein, the term "hydrated" in reference to a composite material refers to composite material that comprises water. Accordingly, in some embodiments, the composite material is hydrated and comprises from about 5% to about 95% of water. The water content of a hydrated composite material can be based on the ratio of weight of water in the composite material to the total weight of the hydrated composite material. Alternatively, the water content of a hydrated composite material can be based on the ratio of weight of water in the composite material to the weight of the composite material before hydration. In some embodiments, water content of a composite material is in reference to the total amount of the carbohydrate or protein in the composite material.

The saturation of the composite material with water can reduce the ultimate strength of the composite material by at least 10%, at least 20%, at least 30%, at least 40%, at least 50%, at least 60%, at least 70%, at least 80%, at least 90%, at least 95%, at least 1-fold, at least 5-fold, at least 10-fold, at least 20-fold, at least 30-fold, at least 40-fold, at least 50-fold, at least 100-fold or more compared to the ultimate strength of the dried composite material.

The inventors have also discovered that a significant difference between the water saturated composite material and the dry counterpart is the homogenization of the former; there is no significant mechanical difference between them. Without wishing to be bound by theory, changes introduced for the water annul other kind of interactions. Moreover, there are no notable differences in the mechanical characteristics of the composite material, carbohydrate and protein hydrated films. Again, without wishing to be bound by theory, the outstanding mechanical characteristics of the composite material result from the different mechanical properties of the components.

In one non-limiting example, the saturation of the chitosan/fibroin composite material with water reduced the ultimate strength to an average value of 3.5 Mpa, which is more than 30 times below that obtained for the dry material. However, the energy absorbed prior to yielding is only reduced by a factor of two; the remaining energy is stored as a significant increase of the elasticity, up to a 23% ultimate strain of its original size, in contrast with the 2.7% for the composite material when dry as shown in FIG. 2D.

IR Spectrometry

IR spectra were obtained with a resolution of 2 cm$^{-1}$ between the 4000 and 500 cm$^{-1}$ (Vertex 70, Bruker, Germany) and analyzed with Essential FTIR (Operant LLC, USA). The Fibroin on composite material FTIR data was obtained by employing the single beam spectra from a Chitosan film as background signal before the Fourier transformation.

Figure 4:
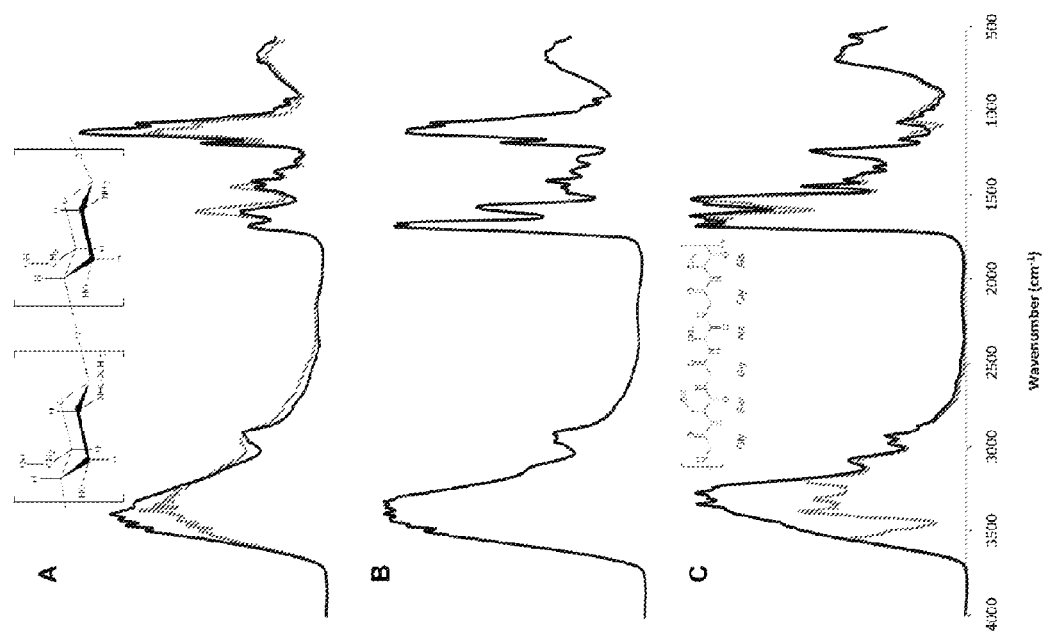
FIG. 4A shows FTIR spectra of Chitosan (black) and protonated Chitosan (grey). Molecule on the top represents the typical Chitosan/Chitin structure, where the acetyl-glucosamine (left) and the glucosamine (right) monomers, are representative of Chitin and Chitosan respectively.
FIG. 4B shows FTIR spectra of the composite laminar material fabricated according to the invention. Both the strong polysaccharide structure of the Chitosan (950-1850 $cm^{-1}$) and the Amide I and II from Fibroin (1640 and 1536 $cm^{-1}$ respectively) are clearly observable.
FIG. 4C shows FTIR specta of Fibroin (black) and Fibroin in the composite laminar material fabricated according to the invention (grey).

From a molecular point of view, Chitin is usually described as cellulose with one hydroxyl group on each monomer substituted with an acetylamine group. FIG. 4 shows the FTIR analysis of Chitosan films and confirms the characteristic absorption of the C=O stretching of the amide (Amide I, 1658 cm$^{-1}$), indicating incomplete deacetylation of the Chitin. The ratio of acetyl groups per glucosamine residues (i.e. degree of acetylation) is calculated as the relative intensity of the absorption bands at both sides of the rocking of the methyl group band (1379 cm$^{-1}$), which are situated at 1321 and 1417 cm$^{-1}$ as shown in FIG. 4. In the Chitosan analyzed in these experiments, 20.3±0.7% of the glucosamine groups were acetylated.

As shown in FIG. 4B, the composite Shrilk material (at a 1:2 Chitosan to Fibroin ratio) shows an IR absorption spectrum very similar to the sum of Chitosan (FIG. 4A, black) and Fibroin (FIG. 4C, black). There is a shift of the amine II band with respect the Chitosan (from 1562 to 1536 cm$^{-1}$), even with a very thin Fibroin layer. This band relates to the mixing between the N—H bending mode, from the amide and amine, and the C—N stretching mode. Therefore, the main interaction between both phases appears to be made through the Nitrogen atom in the number 2 position of the Chitin/Chitosan saccharide ring.

As shown herein, the interaction between the different components in the composite material appears to be restricted to the interface, with the new bonds being screened by signals from the bulk material. To explore the new molecular bonds in detail, the Fibroin spectra in the composite material is shown in grey in FIG. 4C, compared with a single beam spectrum produced by a Chitosan film as background. A comparison with the pure Fibroin films demonstrates an apparent loss in the region around the 3454 cm$^{-1}$ (stretching of the free NH), which support the hypothesis of new bonds being formed with the initially free NH. Moreover, in addition to the modification of the Amide II band already mentioned (because the lost in the absorption band at 1560 cm$^{-1}$), there is a significant decrease in the 1417 cm$^{-1}$ band. The particularity of all the variations of the spectra is that they are located in the same bands altered by the protonation of the amine groups (FIG. 4A, grey) in Chitosan, further suggesting that the bonding between the protein and the Chitosan in the composite laminar material is made specifically through these chemical groups.

This observation can also explain the very poor mechanical characteristics of the Chitosan:Fibroin blend compared to the Shrilk laminate; the Nitrogen atom appears to be directly involved in the crystal structure, through the intermolecular hydrogen bond N—H↔O—C (in the 6th position of the glucosamine) in Chitosan, and through the hydrogen bond between C=O↔H—N (without free OH and NH groups in the bulk crystal) in Chitin. Therefore the interaction with Fibroin is a process that competes with the interchain association of Chitosan and the formation of the crystal structure.

The composite material fabricated in accordance with the present invention is an organic composite laminate material made of biodegradable and biocompatible materials with the strength of the Aluminum alloys but with one half its density. The strength of the composite material is far above the original components and can be formed and adapted for many uses, including both medical and non-medial applications. Additionally it is an excellent model for the study of natural structures with great implications in zoology and material science. Controlling the amount of water in the composite material enables the material to provide a broad range of mechanical characteristics, from a very stiff composite material when dry (Young modulus=5.75±0.48 GPa) to a extremely elastic material when saturated with water (Young modulus=0.017±0.004 GPa).

Uses of the Composite Materials

Due to its biocompatibility, high strength and ability to modulate its stiffness, the composite material can be used in many biomedical applications. For example, the composite material can be used in prosthetic devices, tissue engineering scaffolds, wound healing devices and components as well as a replacement for plastics and other synthetic or inorganic materials. Further, by controlling the water content in the composite material, the stiffness or flexibility of the material can enable it to be used in place of a wide range of tissue types and functions, for example as a scaffold or other prosthetic component. Further, the porous nature of the foam and sponge structural embodiments enables embodiments of the invention to be used for drug and therapeutic agent delivery by incorporating the agent in the pores during or after the fabrication process.

The composite material can also-be used for non-medical applications, e.g. for industrial applications. For example, the composite material can be used anywhere a lightweight high strength material is needed, such as in the automotive (e.g., hybrid vehicles, electric vehicles, and racing vehicles) and aeronautical industries. The composite material can also be used to replace plastics used in the food industry, such as for containers and bottles. The composite material can be used to manufacture consumer goods including, but not limited to, storage containers, luggage, backpacks, tents, clothing, and disposable trash bags. Other exemplary uses of the composite material can include, but are not limited to, bullet proof windows, shatter proof windows, boat sails, parachutes, artillery storage, tires, vehicle bumpers, crash barriers, and road maintenance equipment (e.g., pylons). Additionally, the composite material can be used in manufacturing of components for electronic devices, such as laptops.

The composite material of the present invention has many applications including, for example, drug delivery systems, tissue engineered materials or other biomedical devices. All of the composites described herein can be easily functionalized with drugs, antibiotics, cell responses molecules, dyes, enzymes and other small and large molecules, with retention of function.

The embodiments of the present invention thus provides for composites that may be suitable for a tissue engineered constructs that can be used for defect and organ repair, organ replacement or regeneration strategies that may benefit from these modified silk materials. A composite of the invention can be used for organ repair, organ replacement or regeneration strategies including, but not limited to, spinal disc, cranial tissue, dura, nerve tissue, liver, pancreas, kidney, bladder, spleen, cardiac muscle, skeletal muscle, tendons, ligaments, cornea tissues, and breast tissues. A composite of the invention can be used for defect repair such as hernial repair and wound closure and repair to medical applications. A composite of the material can be used as a full or partial prosthesis and in plastic surgery applications, such as to support reconstruction and to reduce scarring. Any type of cell can be added to the tissue-engineered construct for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells, bone marrow cells, skin cells, pluripotent cells and stem cells (including, e.g., embyonic stems, adult stem cells, and induced pluripotent stem (iPS) cells), and combination thereof, either as obtained from donors, from established cell culture lines, or even before or after molecular genetic engineering. Pieces of tissue can also be used, which may provide a number of different cell types in a single structure.

The composites can be modified to contain at least one active agent. The agent may be mixed with a carbohydrate and/or protein solution prior to forming the composite material, or loaded into the composite material or a portion thereof after it is formed. The agent can also be covalently linked with carbohydrate or protein-layers. For covalent linking, the agent can be linked with the carbohydrate or protein before formation of the composite material. Alternatively, the agent can be covalently linked to the carbohydrate or protein-layer after formation of the composite material. Accordingly, the agent can be directly linked with the carbohydrate or protein-layer with a bond or through an intermediate linker.

The variety of active agents that can be used in conjunction with the composite material of the present invention is vast and can include small molecules, polymers, proteins, peptides, peptidomimimetics, nucleic acids, organic compounds, inorganic compounds, biological compounds, biologically active compounds, compounds having biological activity. For example, the active agent may be a therapeutic agent or biological material, such as cells (including stem cells), proteins, peptides, nucleic acids (DNA, RNA, plasmids, siRNA, antisense oligonucleotides, decoy oligonucleotides, microRNA, aptamers, and ribozymes), nucleic acid analogues, nucleotides, oligonucleotides or sequences, peptide nucleic acids, antibodies, hormones, hormone antagonists, growth factors or recombinant growth factors and fragments and variants thereof, cytokines, or enzymes, antibiotics, viruses, antivirals, toxins, prodrugs, chemotherapeutic agents, small molecules, drugs and combinations thereof. Some exemplary active agents suitable for modifying the composite materials of the present invention includes cells (including stem cells), erythropoietin (EPO), YIGSR peptides, glycosaminoglycans (GAGs), hyaluronic acid (HA), integrins, selectins and cadherins; analgesics and analgesic combinations; steroids; antibiotics; insulin; interferons $\alpha$ and $\gamma$; interleukins; adenosine; chemotherapeutic agents (e.g., anticancer agents); tumor necrosis factors $\alpha$ and $\beta$; antibodies; cell attachment mediators, such as RGD or integrins, or other naturally derived or genetically engineered proteins, polysaccharides, glycoproteins, cytotoxins, prodrugs, immunogens, or lipoproteins.

Other exemplary therapeutic agents include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of The Merck Index, the complete content of all of which are herein incorporated in its entirety.

Other material to be embedded in composite materials can include liposomes and related systems for delivery of genetic materials; peptides and proteins to active cellular signaling cascades; peptides and proteins to promote mineralization or related events from cells; adhesion peptides and proteins to improve film-tissue interfaces; antimicrobial peptides; proteins and related compounds; and carbohydrates, including, for example, glycosaminoglycans and proteoglycans.

As noted, one or more active agents can be used to modify the composite material. Accordingly, when using the composite of the present invention as a platform to support biological material such as cells, it can be desirable to add other materials to promote the growth of the agent, promote the functionality of the agent after it is released from the composite, or increase the agent's ability to survive or retain its efficacy during the processing period. Exemplary materials known to promote cell growth include, but not limited to, cell growth media, such as Dulbecco's Modified Eagle Medium (DMEM), fetal bovine serum (FBS), non-essential amino acids and antibiotics, and growth and morphogenic factors such as fibroblast growth factor (e.g., FGF 1-9), transforming growth factors (TGFs), vascular endothelial growth factor (VEGF), epidermal growth factor (EGF), platelet derived growth factor (PDGF), insulin-like growth factor (IGF-I and IGF-II), bone morphogenetic growth factors (e.g., BMPs 1-7), bone morphogenetic-like proteins (e.g., GFD-5, GFD-7, and GFD-8), transforming growth factors (e.g., TGF-$\alpha$, TGF-$\beta$ I-III), nerve growth factors, and related proteins. Growth factors are known in the art, see, e.g., Rosen & Thies, Cellular & Mol. Basis. Bone Formation & Repair (R.G. Landes Co.).

Enzymatic Bonding to Extracellular Matrix

In another aspect the invention provides a method of attaching a medical implant device to a tissue or organ. The method comprising applying an effective amount of a transglutaminase to the surface of the tissue or organ where the medical implant device needs to be attached and contacting the medical implant device to the surface of the tissue. Alternatively, or in addition, the transglutaminase can be applied to a surface of the medical implant device and the medical implant device contacted with the tissue surface. Still, in another embodiment, the medical implant device can be contacted with the tissue surface and the transglutaminase applied afterwards.

As used herein, in context of applying a transglutaminase, the term "applying" refers to increasing the amount or activity of a transglutaminase at the desired site. Accordingly, the term "applying" embraces topical applications of transglutaminase to a surface, increasing the expression of a host transglutaminase at the site of attachment, and/or increasing the activity of a transglutaminase at the site of attachment. Without wishing to be bound by a theory, one can increase the expression or activity of a host transglutaminase by applying a composition that increases the expression and/or activity of the transglutaminase. For example, Davies et al. (J. Biol. Chem. (1985) 260:5166-5174) describe inducing transglutaminase expression using retinoic acid. Exemplary transglutaminase activators include, but are not limited to, thrombin, TIG3 protein, calcium chloride, and sphingosylphosphorylcholine. Additionally, Sigma-Aldrich sells the Transglutaminase Assay Kit which can be used for screening activators of transglutaminase.

As used herein, by "transglutaminase" is meant a member of the group of enzymes identified by Enzyme Commission System of Classification No. 2.3.2.13 (EC 2.3.2.13). Skilled artisan is well aware that transglutaminases are enzymes that catalyze an acyl transfer reaction of a $\gamma$-carboxamide group of a glutamine residue in a peptide chain. Transglutaminases form $\in$-($\gamma$-Glu)-Lys crosslinks in and between protein molecules when an $\in$-amino group of a lysine residue in a protein acts as an acyl receptor. Transglutaminases can also deaminate a glutamine residue into a glutamic acid residue when water acts as an acyl receptor.

Such transglutaminases include calcium-independent transglutaminases and calcium-dependent transglutaminases. The former include an enzyme derived from microorganisms (see, for example, JP-A-1-27471, content of which is incorporated herein by reference in its entirety), and the latter include an enzyme derived from the guinea pig's liver (see, JP-B-150382, content of which is incorporated herein by reference in its entirety), an enzyme derived from fish (see, for example, Seki Nobuo et al. *Nihon Suisan Gakkaishi*, vol. 56, No. 1, p. 125 (1990), content of which is incorporated herein in its entirety), and the like. Further, it includes enzymes produced by gene recombination (see, JP-A-1-300889, JP-A-5-199883, JP-A-6-225775, contents of which are incorporated herein by reference in their entireties).

The transglutaminase for use in the methods of the present invention can be from a natural or a synthetic source, e.g., recombinant. Thus, transglutaminase prepared (i.e. extracted) from mammalian tissue samples, as well as mammalian transglutaminases expressed by recombinant means are included herein. Furthermore, variants of naturally-occurring mammalian transglutaminases are also included.

In some embodiments, the transglutaminase is a mammalian transglutaminase. Mammalian transglutaminases can be obtained from animal cells and tissues and cellular products.

In some embodiments, transglutaminase is a tissue transglutaminase (tTgase).

In some embodiments, transglutaminase is a microbial transglutaminase. A microbial transglutaminase can be isolated from one or more of a *Streptomyces hygroscopicus* strain, *Streptoverticillium Baldaccii*, *Streptoverticillium mobaraense*, or *Escherichia Coli*. See for example, Cui L et al., Bioresource Technology (2008) 99(9): 3794-3800, content of which is incorporated herein by reference in its entirety).

In some embodiments, transglutaminase is a human transglutaminase. Human transglutaminase can be prepared from human tissue or cells. For example, a human transglutaminase can be extracted from human tissue sources such as lung, liver, spleen, kidney, heart muscle, skeletal muscle, eye lens, endothelial cells, erythrocytes, smooth muscle cells, bone and macrophages.

Alternatively, human transglutaminase can be obtained from a culture of human cells that express a mammalian transglutaminase, using cell culture methodology well known in the art. Preferred cell line sources of such transglutaminases include, but are not limited to, human endothelial cell line ECV304 (for tissue transglutaminase) and human osteosarcoma cell line MG63.

In some embodiments, transglutaminase is a calcium-independent transglutaminase. In some other embodiments, transglutaminase is a calcium-dependent transglutaminase.

Some exemplary transglutaminases include, but are not limited to, Factor XIII A (fibrin stabilizing factor), Type 1 transglutaminase (keratinocyte transglutaminase,), Type 2 transglutaminase (tissue transglutaminase), Type 3 transglutaminase (epidermal transglutaminase), Type 4 transglutaminase (prostate transglutaminase), Type 5 transglutaminase (Transglutaminase X), Type 6 transglutaminase (Transglutaminase Y), and Type 7 transglutaminase (Transglutaminase Z).

It will be appreciated by those skilled in the art that the source of the transglutaminase can be selected according to the particular use (e.g. site of implantation) of the medical implant material. For example, if the medical implant material is to be used as artificial bone, it can be beneficial for the material to comprise a bone-derived transglutaminase. Thus, in the method of the present invention, any of transglutaminases can be used, and the origin and the production process thereof are not limited.

The transglutaminase can be derived from mammals or microorganisms. Moreover, humanized recombinant transglutaminase can also be used.

Some commercially available transglutaminases derived from mammals, such as guinea pig liver-derived transglutaminase, goat-derived transglutaminase and rabbit-derived transglutaminase, are available from Oriental Yeast Co., Ltd., Upstate USA Inc. and Biodesign International. Other non-limiting examples of commercially available transglutaminase products include those produced by Ajinomoto Co. (Kawasaki, Japan), such as Activa TG-TI, Activa TG-FP, Activa TG-GS, Activa TG-RM, and Activa MP; and those produced by Yiming Biological Products Co. (Jiangsu, China), such as TG-B and TG-A.

The transglutaminase can be applied in any suitable form including, but not limited to, solutions, emulsions (oil-in-water, water-in-oil), aerosols, foams, ointments, pastes, lotions, powders, gels, hydrogels, hydrocolloids, creams, and any combinations thereof. In one embodiment, the transglutaminase is applied in the form of a powder.

The transglutaminase can optionally be in a pharmaceutical acceptable composition. A pharmaceutically acceptable composition comprises a transglutaminase formulated together with one or more pharmaceutically acceptable carriers (additives) and/or diluents. As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Generally, the transglutaminase activity is enhanced at elevated temperature. Thus, the bonding can be performed at any temperature. In some embodiments, the bonding is performed at an elevated temperature e.g., 30° C. or higher, 35° C. or higher, 40° C. or higher, 45° C. or higher, 50° C. or higher, 55° C. or higher, or 60° C. or higher. In some embodiments, bonding is performed at room temperature, e.g., from about 15° C. to about 25° C. In some embodiments, bonding is performed at a temperature of about 20° C. to about 30° C.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutically acceptable composition can also include any co-factors, such as salts, for the transglutaminase.

In some embodiments, the transglutaminase can be associated with the medical implant device before the medical implant device is affixed to a tissue or organ. As used in the context of a medical implant device and transglutaminase, the term "associated with" means that the transglutaminase is coated on or otherwise linked (covalently or non-covalently) with the medical implant device. In some embodiments, the transglutaminase can be dispersed in the material used to fabricate the medical implant device. In some embodiments, transglutaminase can be covalently linked to the surface of the medical implant device. In some embodiments, transglutaminase can be non-covalently linked to the surface of the medical implant device.

In some embodiments, transglutaminase can be added to the medical implant device after the medical implant has been fabricated. This can be accomplished, for example, by dipping the fabricated medical implant device in a solution of transglutaminase.

Attachment of a medical implant device comprising a transglutaminase may or may not require application of any additional transglutaminase to the surface of tissue or organ where attachment is to occur.

As used herein, an "effective amount of a transglutaminase" means the amount of transglutaminase which is effective to link a medical implant device to a tissue or organ. Accordingly, in some embodiments, effective amount of a transglutaminase is from about 1 µg to about 100 mg per $cm^2$ of contact surface area. In some embodiments, effective amount of a transglutaminase is selected from the group consisting of from about 1 mg to about 50 mg per $cm^2$, from about 5 mg to about 40 mg per $cm^2$, from about 10 mg to about 30 mg per $cm^2$, from about 15 mg to about 25 mg per $cm^2$, or about 20 mg per $cm^2$. By "contact surface area" is meant the surface area of the tissue that will be in contact with the implant device. For wounds, the contact surface area can mean the size of the wound and/or the total exposed area of the wound.

As used herein, the term "medical implant device" refers to devices for implementation into a subject's body. Exemplary medical implant devices include, but are not limited to, artificial tissues, artificial organs, prosthetic devices, drug delivery devices, wound dressings, fibers, nanoparticles, microparticles, foams, and sponges. Without limitations, a medical implant device can be in any form including, but not limited to 3-D scaffolds, fibers, foams, sponges, films, and any combinations thereof. A medical implant device can be used for permanent substitution of an organ (function).

In some embodiments, the medical implant device is a foam or sponge.

In some embodiments, the medical implant device comprises a nanoparticle or a microparticle.

In one embodiment, the medical implant device is a wound dressing. Exemplary wound dressings include, but are not limited to bandages, gauzes, tapes, meshes, nets, adhesive plasters, films, membranes, and patches. In some embodiments, a wound dressing can comprise a composite material described herein.

In some embodiments, the medical implant device is not a gel.

In some embodiments, the medical implant device is associated with a protein which is cross-linkable by a transglutaminase. As used in context of a medical implant device, the term "associated with" refers to a medical implant device which is coated with, includes, or comprises a transglutaminase linkable protein. In some embodiments, the medical implant device is coated with the transglutaminase linkable protein. By "coated" is meant that the transglutaminase linkable protein is applied to the surface of the medical implant device. Thus, the medical implant device can be painted or sprayed with a solution comprising a transglutaminase linkable protein. Alternatively, the medical implant device can be dipped in a solution of transglutaminase linkable protein solution.

The transglutaminase linkable protein can be covalently or non-covalently associated with the medical implant device, e.g. at the external surface of the medical implant device. Once associated with the medical implant device, the transglutaminase linkable protein provides means of attaching the medical implant device to a tissue or organ.

As used herein, the term "cross-linkable by a transglutaminase" refers to a protein or polypeptide which serves as a substrate for a transglutaminase.

Accordingly, a transglutaminase cross-linkable protein is or comprises a transglutaminase substrate. As used herein, the term "transglutaminase substrate" refers to a peptide or polypeptide sequence with an appropriate transglutaminase target for cross-linking. Without limitations, a transglutaminase linkable protein is or comprises a transglutaminase substrate selected from the group consisting of aldolase A, glyceraldehyde-3-phosphate dehydrogenase, phosphorylase kinase, crystallins, glutathione S-transferase, actin, myosin, troponin, β-tublin, tau, rho, histone, α-oxoglutarate dehydrogenase, β-lactoglobulin, cytochromes, erythrocyte band III, CD38, acetylcholine esterase, collagen, entactin, fibronectin, fibrin, silk, fibroin, fibrinogen, vitronectin, osteopontin, nidogen, laminin, LTBP-1, osteonectin, osteopontin, osteocalcin, thrombospondin, substance P, phospholipases $A_2$, midkine, wheat gelatin, whey proteins, casein, soy proteins, pea legumin, *Candida albicans* surface proteins, HIV envelop glycoproteins gp120 and gp41, HIV aspartyl proteinase, hepatitis C virus core protein, fragments thereof that are capable of binding to a transglutaminase, and combinations thereof. In some embodiments, the transglutaminase linkable protein is silk fibroin or a fragment thereof that is capable of being cross-linked by a transglutaminase.

Peptide and polypeptide sequences with an appropriate transglutaminase target for cross-linking are known in the art. Non-limiting examples of such peptides are described, for example in U.S. Pat. No. 5,428,014; U.S. Pat. No. 5,939,385; and U.S. Pat. No. 7,208,171, content of all of which is incorporated herein by reference. U.S. Pat. No. 5,428,014 describes biocompatible, bioadhesive, transglutaminase cross-linkable polypeptides wherein transglutaminase is known to catalyze an acyl-transfer reaction between the γ-carboxamide group of protein-bound glutaminyl residues and the ∈-amino group of Lys residues, resulting in the formation of ∈-(γ-glutamyplysine isopeptide bonds. U.S. Pat. No. 5,939,385 describes biocompatible, bioadhesive transglutaminase cross-linkable polypeptides.

U.S. Pat. No. 7,208,171, describes the rational design of transglutaminase substrate peptides. The design strategy was based on maximizing the number of available acyl acceptor lysine-peptide substrates and acyl donor glutaminyl-peptide substrates available for transglutaminase cross-linking. Beyond this, the Lys and Glu substrate peptides were designed to possess basic features of known biomacromolecular and synthetic peptide substrates of transglutaminase. For example, the Glu substrate peptides contained 2-5 contiguous Glu residues, based on evidence that peptides become better transglutaminase substrates with increasing length of Glu repeats and that proteins containing two or more adjacent Glu residues are known to be good substrates. A Leu residue was placed adjacent to the Glu near the C-terminus in several peptides, because this has been shown to result in a significant increase in Glu specificity. Regarding the Lys substrate peptides, it has been shown that the composition and sequence of the amino acids adjacent to lysine residues in peptide and protein substrates can have an effect on the amine specificity. Finally, in all peptides a Gly residue was added on the C-terminal side to act as a spacer between the peptide and the polymer in the peptide-polymer conjugates, so that the peptide in the conjugate may be more accessible to enzyme.

A medical implant device can be fabricated from any biocompatible material. As used herein, the term "biocompatible material" refers to any polymeric material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include derivatives and copolymers of a polyimides, poly(ethylene glycol), polyvinyl alcohol, polyethyleneimine, and polyvinylamine, polyacrylates, polyamides, polyesters, polycarbonates, and polystyrenes.

In some embodiments, the medical implant device is fabricated from a material selected from the group consisting of carbohydrate polymers, proteins, silk fibroin, polydimethylsiloxane, polyimide, polyethylene terephthalate, polymethylmethacrylate, polyurethane, polyvinylchloride, polystyrene polysulfone, polycarbonate, polymethylpentene, polypropylene, a polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

A medical implant device can be fabricated from a biodegradable material, e.g., a biodegradable polymer. As used herein, the term "biodegradable" describes a material which can decompose under physiological conditions into breakdown products. Such physiological conditions include, for example, hydrolysis (decomposition via hydrolytic cleavage), enzymatic catalysis (enzymatic degradation), and mechanical interactions. As used herein, the term "biodegradable" also encompasses the term "bioresorbable", which describes a substance that decomposes under physiological conditions to break down to products that undergo bioresorption into the host-organism, namely, become metabolites of the biochemical systems of the host organism.

The term "biodegradable polymer", as used herein, refers to a polymer that at least a portion thereof decomposes under physiological conditions. The polymer can thus be partially decomposed or fully decomposed under physiological conditions.

Exemplary biodegradable polymers include, but are not limited to, polyanhydrides, polyhydroxybutyric acid, polyorthoesters, polysiloxanes, polycaprolactone, poly(lactic-co-glycolic acid), poly(lactic acid), poly(glycolic acid), and copolymers prepared from the monomers of these polymers.

In some embodiments, the medical implant device is fabricated from a biocompatible, biodegradable material.

Suitable polymers which can be used for fabricating a medical implant device include, but are not limited to, one or a mixture of polymers selected from the group consisting of carbohydrate polymers; silk; glycosaminoglycan; fibrin; poly-ethyleneglycol (PEG); C2 to C4 polyalkylene glycols (e.g., propylene glycol); polyhydroxy ethyl methacrylate; polyvinyl alcohol; polyacrylamide; poly (N-vinyl pyrolidone); poly glycolic acid (PGA); poly lactic-co-glycolic acid (PLGA); poly e-carpolactone (PCL); polyethylene oxide; poly propylene fumarate (PPF); poly acrylic acid (PAA); hydrolysed polyacrylonitrile; polymethacrylic acid; polyethylene amine; polyanhydrides; polyhydroxybutyric acid; polyorthoesters; polysiloxanes; polycaprolactone; poly(lactic-co-glycolic acid); poly(lactic acid); poly(glycolic acid); alginic acid; esters of alginic acid; pectinic acid; esters of pectinic acid; carboxy methyl cellulose; hyaluronic acid; esters of hyaluronic acid; heparin; heparin sulfate; chitosan; carboxymethyl chitosan; chitin; pullulan; gellan; xanthan; collagen; carboxymethyl starch; carboxymethyl dextran; chondroitin sulfate; cationic guar; cationic starch as well as salts and esters thereof.

In some embodiments, the medical implant device is fabricated from a carbohydrate polymer. In one embodiment, the carbohydrate polymer is chitosan or derivatives thereof.

In some embodiments, the medical implant device is fabricated from a transglutaminase linkable protein.

In some embodiments, the medical implant device is fabricated from a composite material described herein.

Optionally, a wound healing agent can also be administered to the subject. In some embodiments, the medical implant device comprises the wound healing agent. Without wishing to be bound by a theory, a wound healing agent can be released from the medical implant device over a period of time.

As used herein, a "wound healing agent" is a compound or composition that actively promotes wound healing process. Exemplary wound healing agents include, but are not limited to dexpanthenol; growth factors; enzymes, hormones; povidon-iodide; fatty acids; anti-inflammatory agents; antibiotics; antimicrobials; antiseptics; cytokines; thrombin; angalgesics; opioids; aminoxyls; furoxans; nitrosothiols; nitrates and anthocyanins; nucleosides, such as adenosine; and nucleotides, such as adenosine diphosphate (ADP) and adenosine triphosphate (ATP); neutotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP); nitric oxide; and any combinations thereof.

Exemplary growth factors include, but are not limited to, fibroblast growth factor (FGF), FGF-1, FGF-2, FGF-4, FGF-α, FGF-β, plateletderived growth factor (PDGF), insulin-binding growth factor (IGF), IGF-1, IGF-2, heparin-binding growth factor-1, heparin-binding growth factor-2, epidermal growth factor (EGF), transforming growth factor (TGF), TGF-α, TGF-β, cartilage inducing factors-A and -B, osteoid-inducing factors, osteogenin, vascular endothelial growth factor, bone growth factors, collagen growth factors, insulin-like growth factors, and their biologically active derivatives.

The method of attaching a medical implant device to a tissue or organ can also be used for wound healing. Accordingly, the invention provides a method of promoting wound healing in a subject in need thereof, comprising contacting a transglutaminase to wound surface and contacting a wound dressing to the wound. The wound dressing can be used to cover and close the wound. Method and compositions described herein can be used for suture-less closure of wounds.

As used herein, the term "wound" refers to physical disruption of the continuity or integrity of tissue structure caused by a physical (e.g., mechanical) force, a biological (e.g., thermic or actinic force), or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. In particular, the term encompasses ulcerations (i.e., ulcers), preferably ulcers of the skin. The term "wound" also includes surgical wounds.

As used herein, the term "wound healing" refers to a regenerative process with the induction of an exact temporal and spatial healing program comprising wound closure and the processes involved in wound closure. The term "wound healing" encompasses but is not limited to the processes of granulation, neovascularization, fibroblast, endothelial and epithelial cell migration, extracellular matrix deposition, reepithelialization, and remodeling. The term "wound healing" includes the restoration of tissue integrity. It will be understood that this can refer to a partial or a full restoration of tissue integrity. Treatment of a wound thus refers to the promotion, improvement, progression, acceleration, or otherwise advancement of one or more stages or processes associated with the wound healing process.

As used herein, the term "wound closure" refers to the healing of a wound wherein sides of the wound are rejoined to form a continuous barrier (e.g., intact skin).

As used herein, the term "granulation" refers to the process whereby small, red, grain-like prominences form on a raw surface (that of wounds) as healing agents.

As used herein, the term "neovascularization" refers to the new growth of blood vessels with the result that the oxygen and nutrient supply is improved. Similarly, the term "angiogenesis" refers to the vascularization process involving the development of new capillary blood vessels.

As used herein, the term "cell migration" refers to the movement of cells (e.g., fibroblast, endothelial, epithelial, etc.) to the wound site.

As used herein, the term "extracellular matrix deposition" refers to the secretion by cells of fibrous elements (e.g., collagen, elastin, reticulin), link proteins (e.g., fibronectin, laminin), and space filling molecules (e.g., glycosaminoglycans).

As used herein, the term "re-epithelialization" refers to the reformation of epithelium over a denuded surface (e.g., wound).

As used herein the term "remodeling" refers to the replacement of and/or devascularization of granulation tissue.

The wound can be acute or chronic. As used herein, the term "chronic wound" refers to a wound that does not fully heal even after a prolonged period of time (e.g., 2 to 3 months or longer). Chronic wounds, including pressure sores, venous leg ulcers and diabetic foot ulcers, can simply be described as wounds that fail to heal. Whilst the exact molecular pathogenesis of chronic wounds is not fully understood, it is acknowledged to be multi-factorial. As the normal responses of resident and migratory cells during acute injury become impaired, these wounds are characterized by a prolonged inflammatory response, defective wound extracellular matrix (ECM) remodelling and a failure of re-epithelialisation.

The wound can be an internal wound, e.g. where the external structural integrity of the skin is maintained, such as in bruising or internal ulceration, or external wounds, particularly cutaneous wounds, and consequently the tissue can be any internal or external bodily tissue. In some embodiment the tissue is skin (such as human skin), i.e. the wound is a cutaneous wound, such as a dermal or epidermal wound.

Wounds can be classified in one of two general categories, partial thickness wounds or full thickness wounds. A partial thickness wound is limited to the epidermis and superficial dermis with no damage to the dermal blood vessels. A full thickness wound involves disruption of the dermis and extends to deeper tissue layers, involving disruption of the dermal blood vessels. The healing of the partial thickness wound occurs by simple regeneration of epithelial tissue. Wound healing in full thickness wounds is more complex.

In some embodiments, the wound is selected from the group consisting of cuts and lacerations, surgical incisions or wounds, punctures, grazes, scratches, compression wounds, abrasions, friction wounds (e.g. nappy rash, friction blisters), decubitus ulcers (e.g. pressure or bed sores); thermal effect wounds (burns from cold and heat sources, either directly or through conduction, convection, or radiation, and electrical sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g. psoriasis and eczema, stomach or intestinal ulcers, oral wounds, including a ulcers of the mouth, damaged cartilage or bone, amputation wounds, corneal lesions, and any combinations thereof.

A medical implant device comprising a transglutaminase can be used to treat hemorrhage, stop internal or external bleeding. Accordingly, the invention provides a method of treating, stopping, or decreasing hemorrhage or internal bleeding or external bleeding, the method comprising applying a medical implant device comprising a transglutaminase at the site of hemorrhage or bleeding.

Bonding of Scaffolds

In another aspect the invention provides a method of bonding or attaching two scaffolds together, e.g., two different scaffolds or different parts of one larger structure. The method comprising applying an effective amount of a transglutaminase to a surface of a first scaffold where a second scaffold needs to be attached and contacting the second scaffold to the surface of the first scaffold. Alternatively, or in addition, the first scaffold can be contacted with the second scaffold and the transglutaminase applied afterwards. In some embodiments, the transglutaminase is applied to both the first and second scaffolds before contacting them together.

In some embodiments, the transglutaminase can be associated with the first scaffold before contact with the second scaffold. As used in the context of a scaffold and transglutaminase, the term "associated with" means that the transglutaminase is coated on or otherwise linked (covalently or non-covalently) with the scaffold. In some embodiments, the transglutaminase can be dispersed in the material used to fabricate the scaffold. In some embodiments, transglutaminase can be covalently linked to the surface of the scaffold. In some embodiments, transglutaminase can be non-covalently linked to the surface of the scaffold. In some embodiments, the transglutaminase can be associated with the first scaffold and the second scaffold before contacting them together.

In some embodiments, transglutaminase can be added to a scaffold after the scaffold has been fabricated. This can be accomplished, for example, by dipping the fabricated scaffold in a solution of transglutaminase. Attachment of a scaffold comprising a transglutaminase may or may not require application of any additional transglutaminase to the surface of the scaffold where attachment is to occur.

In context of attaching two scaffolds together, an "effective amount of a transglutaminase" means the amount of transglutaminase which is effective to link the tewo scaffolds together. In this context, effective amount can range from about 1 µg to about 100 mg per cm$^2$ of contact surface area. In some embodiments, effective amount of a transglutaminase is from about 1 mg to about 50 mg per cm$^2$, from about 5 mg to about 40 mg per cm$^2$, from about 10 mg to about 30 mg per cm$^2$, from about 15 mg to about 25 mg per cm$^2$, or about 20 mg per cm$^2$.

As used herein, the term "scaffold" refers to any 3-dimensional object. Exemplary scaffolds include, but are not limited to, artificial tissues, artificial organs, prosthetic devices, drug delivery devices, wound dressings (e.g., bandages, gauzes, tapes, meshes, nets, adhesive plasters, films, membranes, patches, and the like), fibers, films, foams, sponge, nanoparticles, microparticles, and any combinations thereof.

In some embodiments, a scaffold is associated with a protein which is cross-linkable by a transglutaminase. As used in context of a scaffold, the term "associated with" refers to a scaffold which is coated with, includes, or comprises a transglutaminase linkable protein. In some embodiments, the scaffold is coated with the transglutaminase linkable protein. By "coated" is meant that the transglutaminase linkable protein is applied to the surface of the scaffold. Thus, the scaffold can be painted or sprayed with a solution comprising a transglutaminase linkable protein. Alternatively, the scaffold can be dipped in a solution of transglutaminase linkable protein solution.

The transglutaminase linkable protein can be covalently or non-covalently associated with the scaffold, e.g. at the external surface of the scaffold. Once associated with the scaffold, the transglutaminase linkable protein provides means of attaching the scaffold to a second scaffold and/or a tissue or organ.

A scaffold can be fabricated from any biocompatible and/or biodegradable material. In some embodiments, the scaffold is fabricated from a carbohydrate polymer. In one embodiment, the scaffold is fabricated from chitosan or derivatives thereof. In some embodiments, the scaffold is fabricated from a composite material described herein.

In some embodiments, the scaffold is fabricated from a transglutaminase linkable protein.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not. The terms "comprising" and "comprises" include the terms "consisting of" and "consisting essentially of."

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects)

resulting from administration of the treatment. "Less effective" means that the treatment results in a therapeutically significant lower level of pharmacological effectiveness and/or a therapeutically greater level of adverse physiological effects.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

The invention can be defined by any of the following numbered paragraphs:

1. A composite laminar material comprising a carbohydrate based substrate and a protein.
2. The composite laminar material of paragraph 1 wherein the carbohydrate based substrate comprises a film, a fiber, a sponge, a mesh, a foam, or a nanoscale structure.
3. The composite laminar material of any of paragraphs 1-2, wherein the ratio of carbohydrate to protein is in the range of 10:1 to 1:10.
4. The composite laminar material of any of paragraphs 1-3, wherein carbohydrate based substrate is a chitin, fructooligosaccharide, galactooligosaccharides, mannanoligosaccharides, glycogen, starch (amylase, amylopectin), glycosaminoglycans (e.g., hyaluronic acid, chondroitin-4-sulfate, chondroitin-6-sulfate, dermatan sulfate, keratin sulfate, heparin and the like), cellulose, beta-glucan (zymosan, lentinan, sizofiran), maltodextrin, inulin, or levan beta (2→6) based substrate.
5. The composite laminar material of any of paragraphs 1-4, wherein the carbohydrate based substrate is a Chitosan based substrate.
6. The composite laminar material of any of paragraphs 1-5, wherein the protein is selected from the group consisting of silk fibroin, perculin, abductin, elastin, resilin, fibronectin, fibrinogen, keratin, titin, collagen, actin, Arp2/3, coronin, dystrophin, FtsZ, myosin, spectrin, Tau (protein), tubulin, F-spondin, Pikachurin, fragments and analogs and derivatives thereof, and any combinations thereof.
7. The composite laminar material of paragraph 1, wherein the carbohydrate is Chitosan and the protein includes silk fibroin and the ratio of Chitosan to silk fibroin is in the range of 1:1.5 to 1:2.
8. The composite laminar material of any of paragraphs 1-7, wherein the carbohydrate based substrate includes at least one surface having a predefined microtopography and the protein is applied to the surface.
9. The composite laminar material of paragraph 8, wherein the predefined microtopography is molded into the carbohydrate-based substrate.
10. The composite laminar material of any of paragraphs 1-9, wherein the protein includes at least one surface having a predefined microtopography.
11. The composite laminar material of paragraph 10, wherein the predefined microtopography is molded into the protein.
12. The composite laminar material of any of paragraphs 1-11 further comprising a second carbohydrate based substrate.
13. The composite laminar material of paragraph 12, wherein the second carbohydrate based substrate is a chitin based substrate.
14. The composite laminar material of any of paragraphs 1-13, wherein the composite material comprises a molecule selected from the group consisting of carbon fibers, carbon nanotubes, fiberglass, small molecules, polymers, proteins, peptides, peptidomimimetics, nucleic acids, organic compounds, inorganic compounds, crystalline compounds, biological compounds, biologically active compounds, compounds having biological activity, and a biological, a pharmaceutical or a therapeutic agent, and any combinations thereof, in at least one of carbohydrate-layer or protein-layer.
15. The method of paragraph 14, wherein the molecule is in the carbohydrate-layer.
16. The method of paragraph 15, wherein the molecule is covalently linked with the carbohydrate-layer.
17. The method of paragraph 14, wherein the molecule is in the protein-layer.
18. The method of paragraph 17, wherein the molecule is covalently linked with the protein-layer.
19. The composite laminar material of any of paragraphs 14-18, wherein the crystalline material is calcium carbonate.
20. The composite laminar material of any of paragraphs 1-19 further comprising a water repelling coating on at least a portion of the composite material.
21. The composite laminar material of any of paragraphs 20, wherein the composite material is composed of parylene.
22. The composite laminar material of any of paragraphs 20-21, wherein the composite material exhibits variable mechanical properties as a function of a location of the water repelling coating on a portion of the composite material when exposed to aqueous environments.
23. A method of forming a composite laminar material comprising: providing a carbohydrate based substrate and contacting the carbohydrate based substrate with a protein solution.
24. The method of paragraph 23, wherein the carbohydrate based substrate is a chitin, fructooligosaccharide, galactooligosaccharides, mannanoligosaccharides, glycogen, starch (amylase, amylopectin), glycosaminoglycans (e.g., hyaluronic acid, chondroitin-4-sulfate, chondroitin-6-sulfate, dermatan sulfate, keratin sulfate, heparin and the like), cellulose, beta-glucan (zymosan, lentinan, sizofiran), maltodextrin, inulin, or levan beta (2→6) based substrate.
25. The method of any of paragraphs 23-24, wherein the carbohydrate based substrate is a Chitosan based substrate.
26. The method of any of paragraphs 23-25, wherein the protein is selected from the group consisting of silk fibroin, perculin, abductin, elastin, resilin, fibronectin, fibrinogen, keratin, titin, collagen, actin, Arp2/3, coronin, dystrophin, FtsZ, myosin, spectrin, Tau (protein), tubulin, F-spondin, Pikachurin, fragments and analogs and derivatives thereof, and any combinations thereof.

27. The method of any of paragraphs 23-36, wherein the ratio of carbohydrate to protein is in the range of from 10:1 to about 1:10.

28. The method of any of paragraphs 23-27, wherein the carbohydrate based substrate is formed by dehydrating a solution of carbohydrate based material.

29. The method of paragraph 28, wherein the solution of carbohydrate based material includes an acid.

30. The method of paragraph 29, wherein the acid is selected from the group consisting of itaconic acid, polyitaconic acid, acontic acid, uric acid, glucuronic acid, formic acid, acetic acid, trichloroacetic acid, propionic acid, butanoic acid, 4-chlorobutanoic acid, 3-chlorobutanoic acid, 2-bromobutanoic acid, 2-chlorobutanoic acid, chlorous acid, hypochlorous acid, citric acid, gluconic acid, lactic acid, oxalic acid, tartaric acid, ascorbic acid, Meldrum's acid, hydrofluoric acid, hydrocyanic acid, hydrogens sulfide, orthophosphoric acid, sulfurous acid, carbonic acid, conjugate acid of a weak base, and any combinations thereof.

31. The method of any of paragraphs 29-30 further comprising neutralizing the carbohydrate based material by applying a basic solution.

32. The method of paragraph 30, wherein the basic solution comprises a base selected from the group consisting of sodium hydroxide, ammonium hydroxide, potassium hydroxide, calcium hydroxide, magnesium hydroxide, barium hydroxide, strontium hydroxide, lithium hydroxide, rubidium hydroxide, sodium carbonate, and ammonia or the basic solution is a high pH buffer.

33. The method of paragraph 32, wherein the high pH buffer is a carbonate buffer.

34. The method of any of paragraphs 23-33, wherein the carbohydrate based substrate is formed by freeze drying a solution of carbohydrate based material.

35. The method of any of paragraphs 23-33, wherein the carbohydrate based substrate is formed by injecting air bubbles into a solution of carbohydrate based material.

36. The method of any of paragraphs 23-33, wherein the carbohydrate based substrate is formed by spinning a carbohydrate based solution to form fibers.

37. The method of any of paragraphs 23-33 or 35, wherein the carbohydrate based substrate is formed by electrospinning a chitin-based solution to form fibers.

38. The method of any of paragraphs 22-32 or 35, wherein the carbohydrate based substrate is formed by rotary spinning a carbohydrate based solution to form fibers.

39. The method of any of paragraphs 23-38 further comprising inducing a beta transition of the protein.

40. The method paragraph 39, wherein the beta transition is induced by treating the protein with one or more of the following agents including alcohols, organic solvents, aqueous solutions, or the application of stress, pressure or heat.

41. The method of any of paragraphs 23-40 further comprising: introducing carried material selected from the group consisting of carbon nanotubes, fiberglass, small molecules, polymers, proteins, peptides, peptidomimetics, nucleic acids, organic compounds, inorganic compounds, crystalline material, biological compounds, biologically active compounds, compounds having biological activity, and a biological, a pharmaceutical or a therapeutic agent, and any combinations thereof, to the composite material.

42. The method of paragraph 40, wherein the carried material is covalently linked to the composite material.

43. A composition of matter formed by any of the methods of paragraphs 23-42.

44. A prosthetic device comprising a composition of matter formed by any of the methods of paragraphs 23-42.

45. A tissue engineering scaffold comprising a composition of matter formed by any of the methods of paragraphs 23-42.

46. A drug delivery device comprising a composition of matter formed by any of the methods of paragraphs 23-42.

47. An implantable material comprising a composition of matter formed by any of the methods of paragraphs 23-42.

48. A material comprising a composition of matter formed by any of the methods of paragraphs 23-42 comprising minerals or crystal materials.

49. A thin clear film comprising a composition of matter formed by any of the methods of paragraphs 23-42.

50. A multi-laminate material comprising a composition of matter formed by any of the methods of paragraphs 23-42.

51. A multi-laminate material comprising a composition of matter formed by any of the methods of paragraphs 23-42 comprising additional components to provide tailored mechanical properties.

52. A material comprising a composition of matter formed by any of the methods of paragraphs 23-42 comprising a water-repelling coating material.

53. A material comprising a composition of matter formed by any of the methods of paragraphs 23-42 comprising variable regions of a water-repelling coating material to provide regions with variable flexibility.

54. A method of forming a composite laminar material comprising:
dissolving a chitin based material in an acidic solution;
forming a chitin based structure of the chitin based material by evaporating the solvent;
treating the chitin based structure with a base solution to neutralize the protonated amino groups;
washing the chitin based structure;
optionally dehydrating the chitin based structure;
applying a protein solution to the chitin based structure to produce a composite material having at least one layer of protein on the chitin based structure;
drying the protein-layer on the chitin based structure; and
treating the composite material with an alcohol based solution to induce a beta transition of the protein.

55. The method of paragraph 54, wherein the ratio of chitin based material to protein is in the range of from 10:1 to 1:10.

56. The method of any of paragraphs 54-55, wherein the chitin based material is chitosan.

57. The method of any of paragraphs 54-56, wherein the protein is fibroin.

58. The method of any of paragraphs 54-57, wherein the acidic solution includes acetic acid.

59. The method of any of paragraphs 534-58, wherein the base solution includes NaOH.

60. The method of any of paragraphs 54-59, wherein the alcohol based solution includes methanol.

61. A composition of matter formed by any of the methods of paragraphs 54-60.

62. A method of adhering a medical implant device to a tissue or organ, the method comprising applying an effective amount of a transglutaminase to surface of the tissue or organ and contacting the medical implant device to the surface of the tissue.
63. The method of paragraph 62, wherein the medical implant device comprises a transglutaminase.
64. A method of adhering a medical implant device to a tissue or organ, the method comprising contacting the medical implant device with the organ, wherein the medical implant device comprises an effective amount of a transglutaminase.
65. The method of paragraph 65, further comprising applying an effective amount of a transglutaminase to surface of the tissue.
66. The method of any of paragraphs 62-65, wherein the transglutaminase is a mammalian transglutaminase.
67. The method of any of paragraphs 62-65, wherein the transglutaminase is a microbial transglutaminase (mTgase).
68. The method of any of paragraphs 62-67, wherein the transglutaminase is a calcium independent transglutaminase.
69. The method of any of paragraphs 62-68, wherein the transglutaminase is selected from the group consisting of Factor XIII A (fibrin stabilizing factor), Type 1 transglutaminase (keratinocyte transglutaminase,), Type 2 transglutaminase (tissue transglutaminase, tTgase), Type 3 transglutaminase (epidermal transglutaminase), Type 4 transglutaminase (prostate transglutaminase), Type 5 transglutaminase (Transglutaminase X), Type 6 transglutaminase (Transglutaminase Y), Type 7 transglutaminase (Transglutaminase Z), and any combinations thereof.
70. The method of any of paragraphs 62-69, wherein the transglutaminase is formulated in a solution, an emulsion, an aerosol, a foam, an ointment, a paste, a lotion, a powder, a gel, a hydrogel, a hydrocolloid, a microparticle, a nanoparticle, or a cream.
71. The method of any of paragraphs 62-70, wherein the medical implant device is selected from the group consisting of artificial tissues, artificial organs, prosthetic devices, drug delivery devices, wound dressings, films, foams, sponges, hemostatic materials, and any combinations thereof.
72. The method of paragraph 71, wherein the medical implant device is a wound dressing selected from the group consisting of bandages, gauzes, tapes, meshes, nets, adhesive plasters, films, membranes, patches, microparticles, nanoparticles, and any combinations thereof.
73. The method of paragraph 71, wherein the medical implant device is a foam.
74. The method of any of paragraphs 62-73, wherein the medical implant device is comprises a protein and wherein the protein is cross-linkable by a transglutaminase.
75. The method of paragraph 74, wherein the medical implant device is coated with the protein.
76. The method of any of paragraphs 74-75, wherein the protein is a silk fibroin.
77. The method of any of paragraphs 62-76, wherein the transglutaminase is coated on the surface of the medical implant device.
78. The method of any of paragraphs 62-77, wherein the transglutaminase is non-covalently linked with the medical implant device.
79. The method of any of paragraphs 62-78, wherein the effective amount of transglutaminase is from about 1 μg to about 100 mg per cm$^2$ of contact surface area between the tissue or the organ and the medical implant device.
80. The method of any of paragraphs 62-79, further comprising administering a wound healing agent.
81. The method of any paragraph paragraphs 80, wherein the wound healing agent is selected from the group consisting of dexpanthenol; growth factors; enzymes, hormones; povidon-iodide; fatty acids; anti-inflammatory agents; antibiotics; antimicrobials; antiseptics; cytokines; thrombin; angalgesics; opioids; aminoxyls; furoxans; nitrosothiols; nitrates and anthocyanins; nucleosides, such as adenosine; and nucleotides, such as adenosine diphosphate (ADP) and adenosine triphosphate (ATP); neutotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP); nitric oxide; and any combinations thereof.
82. The method of any of paragraph 62-81, wherein the medical implant device is fabricated from a biocompatible, biodegradable material.
83. The method of any of paragraphs 62-82, wherein the medical implant device is fabricated from a composite material of any of paragraphs 1-21.
84. The method of any of paragraphs 62-83, wherein said applying comprises increasing expression or activity of a host transglutaminase.
85. A method of promoting wound healing in a subject in need thereof, comprising applying an effective amount of a transglutaminase to a wound surface and contacting a wound dressing to the wound, wherein the wound dressing comprises a composite material of any of paragraphs 1-21.
86. The method of paragraph 85, further comprising applying a foam to the wound, wherein the foam comprises a composite material of any of paragraphs 1-21.
87. The method of any of paragraphs 85-86, wherein the wound is selected from the group consisting of cuts and lacerations, surgical incisions, punctures, grazes, scratches, compression wounds, abrasions, friction wounds, chronic wounds, ulcers, thermal effect wounds, chemical wounds, wounds resulting from pathogenic infections, skin graft/transplant donor and recipient sites, immune response conditions, oral wounds, stomach or intestinal wounds, damaged cartilage or bone, amputation sites and corneal lesions.
88. The method of any of paragraphs 85-87, wherein the transglutaminase is a mammalian transglutaminase.
89. The method of any of paragraphs 85-87, wherein the transglutaminase is a microbial transglutaminase (mTgase).
90. The method of any of paragraphs 85-89, wherein the transglutaminase is a calcium independent transglutaminase.
91. The method of any of paragraphs 85-90, wherein the transglutaminase is selected from the group consisting of Factor XIII A (fibrin stabilizing factor), Type 1 transglutaminase (keratinocyte transglutaminase,), Type 2 transglutaminase (tissue transglutaminase), Type 3 transglutaminase (epidermal transglutaminase), Type 4 transglutaminase (prostate transglutaminase), Type 5 transglutaminase (Transglutaminase X), Type 6 transglutaminase (Transglutaminase Y), Type 7 transglutaminase (Transglutaminase Z), and any combinations thereof.
92. The method of any of paragraphs 85-91, wherein the transglutaminase is formulated in a solution, an emulsion, an aerosol, a foam, an ointment, a paste, a lotion, a powder, a gel, a hydrogel, a hydrocolloid, a microparticle, a nanoparticle, or a cream.
93. The method of any of paragraphs 85-92, wherein the wound dressing is selected from the group consisting of bandages, gauzes, tapes, meshes, nets, adhesive plasters, films, membranes, patches, and any combinations thereof.
94. The method of any of paragraphs 85-93, wherein the transglutaminase is associated with the wound dressing.
95. The method of paragraph 94, wherein the transglutaminase is coated on the surface of the wound dressing.
96. The method of any of paragraphs 94-95, wherein the transglutaminase is non-covalently linked with the wound dressing.
97. The method of any of paragraphs 85-96, wherein the effective amount of transglutaminase is from about 1 μg to about 100 mg per cm² of wound area.
98. The method of any of paragraphs 85-97, further comprising administering a wound healing agent to the subject.
99. The method of paragraph 98, wherein the wound healing agent is selected from the group consisting of dexpanthenol; growth factors; enzymes, hormones; povidon-iodide; fatty acids; anti-inflammatory agents; antibiotics; antimicrobials; antiseptics; cytokines; thrombin; analgesics; opioids; aminoxyls; furoxans; nitrosothiols; nitrates and anthocyanins; nucleosides; nucleotides; neurotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP); nitric oxide; and any combinations thereof.
100. The method of any of paragraphs 85-99, wherein said applying comprises increasing expression or activity of a host transglutaminase.
101. The method of any of paragraphs 85-99, wherein said applying is before, after or during contacting of the medical implant device or the wound dressing.

To the extent not already indicated, it will be understood by those of ordinary skill in the art that any one of the various embodiments herein described and illustrated can be further modified to incorporate features shown in any of the other embodiments disclosed herein. Thus, other embodiments are within the scope and spirit of the invention. Further, while the description above refers to the invention, the description may include more than one invention.

EXAMPLES

The invention now being generally described, it will be more readily understood by reference to the following examples, which are included merely for purposes of illustration of certain aspects and embodiments of the present invention, and are not intended to limit the invention.

Figure 23:
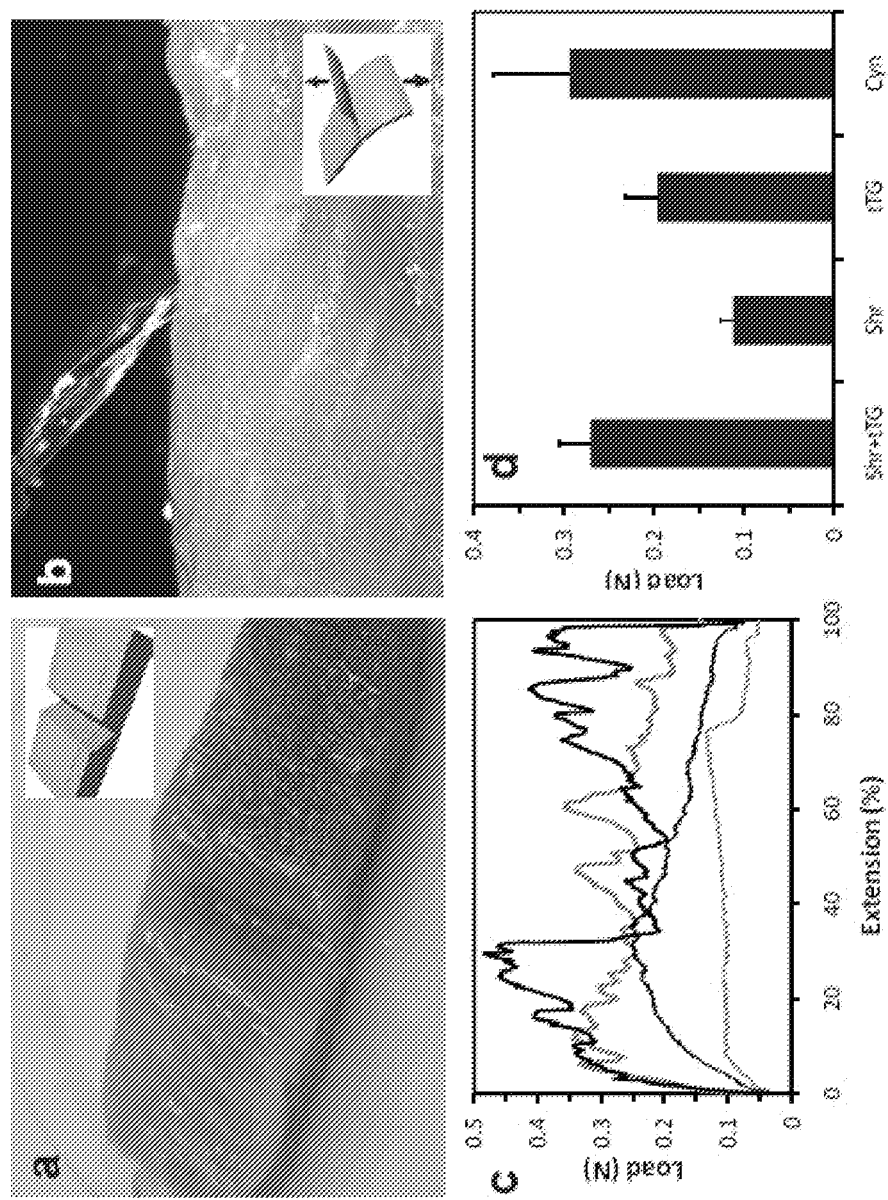
FIGS. 23A-23D show the analysis of the adhesion strength of the films to the biological tissue. The tissue is postmortem domestic pig ("Sus domesticus") lumbar tissue.
Figure 24:
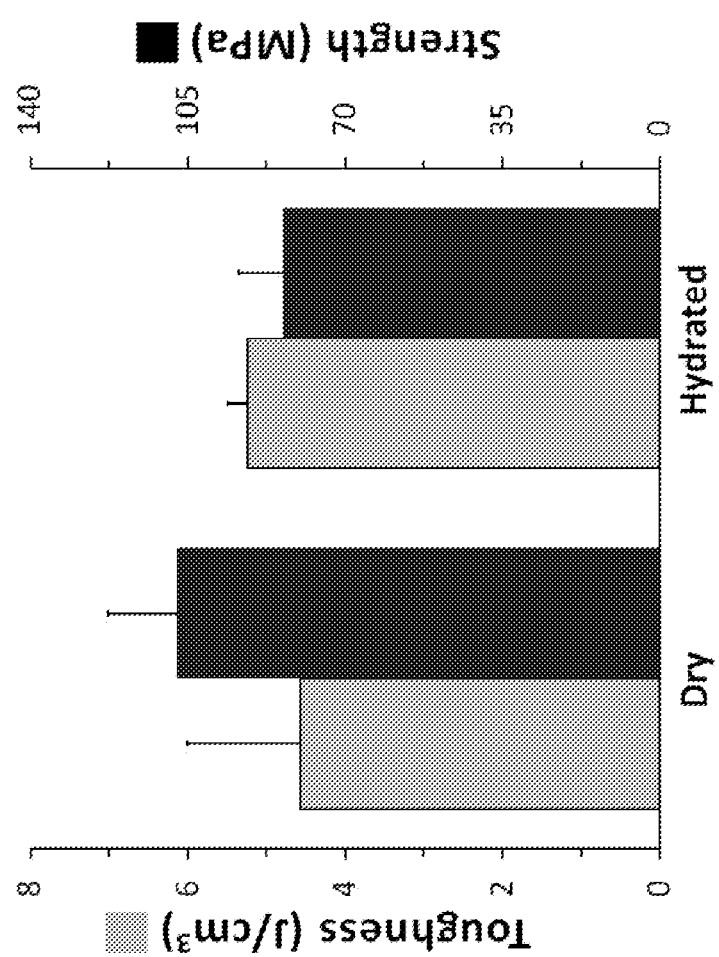
FIG. 24 is a bar graph showing that parylene coating is an effective moisture barrier even in extreme conditions. The dry samples correspond to the plain coated Shrilk (standard conditions) while the "Hydrated" are those in equilibrium with a water based environment (24 h immersion). In that environment and with only a 1 micrometer thick coating the sample strength is of about a 80% (84 MPa) of the strength at standard conditions.

Transglutaminase in powder form was applied at about 20 mg/cm² on the tissue and a hydrated film (either shrilk or a chitosan film) was contacted with the tissue. After 30 minutes of bonding at room temperature, the sample was subjected to a peel test. Results of the peel test are shown in FIG. 23. The inventors discovered that the either side of a shrilk film (carbohydrate layer or the protein layer) can be contacted with the tissue for bonding.

Figure 25:
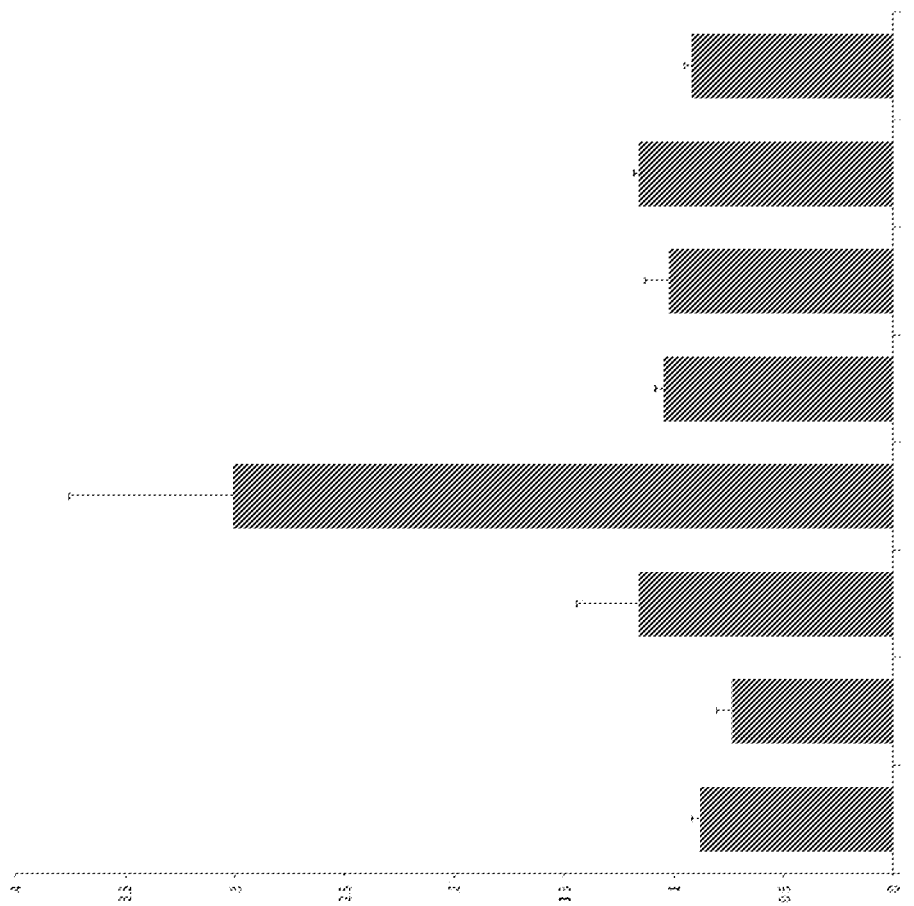
FIG. 25 is a bar graph showing adhesion to dermis tissue (pig). Because the last layer of the epidermis is generated by cornification, which involves the strong (natural) treatment of this layer with transglutaminases. Therefore this layer may be the only tissue in a subject with no available groups for bonding by transglutaminase treatment. Results confirmed this as no bonding by transglutaminases was seen. However, when the last layer is slightly damaged and the second layer exposed, then the bonding by transglutaminases is successful, as demonstrated in experiments where shrilk was bonded to the dermis instead of epidermis.

A similar experiment was carried out to test bonding to dermis tissue. Because the last layer of the epidermis is generated by cornification, this layer may be the only tissue in a subject with no available groups for bonding by transglutaminase treatment. Results confirmed this as no bonding by transglutaminases was seen. However, when the last layer is slightly damaged and the second layer exposed, then the bonding by transglutaminases is successful, as demonstrated in experiments where shrilk was bonded to the dermis instead of epidermis as shown in FIG. 25. This shows that shrilk can be used as a "patch" for treating skin (e.g., bandages).

All patents and other publications identified herein are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A composite laminate material comprising a carbohydrate based layer and a protein based layer, wherein carbohydrate to protein are present in a ratio in the range of 1:1.5 to 1:2.5, where the ratio is based on dry weight or moles of carbohydrate and protein, and wherein chitosan is the carbohydrate in the carbohydrate based layer and silk fibroin is the protein in the protein based layer.

2. The composite laminate material of claim 1 wherein the carbohydrate based layer comprises a film, a fiber, a sponge, a mesh, a foam, or a nanoscale structure.

3. The composite laminate material of claim 1, wherein the ratio of carbohydrate to protein is 1:2, where the ratio is based on dry weight or moles of carbohydrate and protein.

4. The composite laminate material of claim 1, wherein the carbohydrate based layer includes at least one surface having a predefined microtopography and the protein is applied to the surface.

5. The composite laminate material of claim 1, wherein the composite material further comprises a molecule selected from the group consisting of carbon fibers, carbon nanotubes, fiberglass, small molecules, polymers, proteins, peptides, peptidomimimetics, nucleic acids, organic compounds, inorganic compounds, crystalline compounds, biological compounds, and biologically active compounds, and any combinations thereof, in at least one of the carbohydrate layer or the protein layer.

6. The composite laminate material of claim 1 further comprising a water repelling coating on at least a portion of the composite material.

7. The composite laminate material of claim 6, wherein the water repelling coating comprises parylene.

8. A method of forming a composite laminate material comprising:
providing a carbohydrate based layer and neutralizing the carbohydrate based layer with a base solution;
optionally dehydrating the carbohydrate based layer; and
contacting the carbohydrate based layer with a protein solution to produce a composite material; and optionally treating the composite material with an alcohol based solution, and wherein carbohydrate to protein are present in a ratio in the range of 1:1.5 to 1:2.5 and wherein chitosan is the carbohydrate in the carbohydrate based layer and silk fibroin is the protein.

9. A composition of matter formed by a method comprising:

providing a carbohydrate based layer and neutralizing the carbohydrate based layer with a base solution;
optionally dehydrating the carbohydrate based layer; and
contacting the carbohydrate based layer with a protein solution to produce a composite material; and
optionally treating the composite material with an alcohol based solution,
wherein carbohydrate to protein are present in a ratio in the range of 1:1.5 to 1:2.5, and wherein chitosan is the carbohydrate in the carbohydrate based layer and silk fibroin is the protein.

10. A multi-laminate material having the structure [(protein-layer)$_x$:[(carbohydrate-layer)$_y$:(protein-layer)$_z$]$_m$]$_n$, wherein m, n, y, and z are independently an integer equal to or greater than 1; and x is 0 or an integer equal to or greater than 1, and wherein ratio of carbohydrate to protein are present in a ratio in the range of 1:1.5 to 1:2.5, and wherein chitosan is the carbohydrate in the carbohydrate based layer and silk fibroin is the protein in the protein based layer.

11. A method of forming a composite laminate material comprising:
dissolving a chitin based material in an acidic solution;
forming a chitin based structure of the chitin based material by evaporating the solvent;
treating the chitin based structure with a base solution to neutralize protonated amino groups;
washing the chitin based structure;
optionally dehydrating the chitin based structure;
applying a protein solution to the chitin based structure to produce a composite material having at least one layer of protein on the chitin based structure;
drying the protein-layer on the chitin based structure; and
treating the composite material with an alcohol based solution to induce a beta transition of the protein,
wherein a ratio of chitin to protein is 1:1.5 to 1:2.5, where the ratio is based on dry weight or moles of chitin and protein, and wherein chitosan is the chitin in the chitin based layer and silk fibroin is the protein.

12. The composite laminate material of claim 10, wherein the ratio of chitosan to silk fibroin is 1:2.

13. The composite laminate material of claim 1, wherein the ratio of chitosan to silk fibroin is 1:2.

* * * * *